United States Patent
Böhm et al.

(10) Patent No.: US 9,173,595 B2
(45) Date of Patent: Nov. 3, 2015

(54) NON-INVASIVE METHOD AND APPARATUS FOR OPTIMIZING THE RESPIRATION OF ATELECTATIC LUNGS

(75) Inventors: Stephan Böhm, Lauenburg an der Elbe (DE); Gerardo Tusman, Buenos Aires (AR)

(73) Assignee: Stephan Bohm, Lauenburg an der Elbe (DE)

( * ) Notice: Subject to any disclaimer, the term of this patent is extended or adjusted under 35 U.S.C. 154(b) by 1757 days.

(21) Appl. No.: 11/525,244

(22) Filed: Sep. 22, 2006

(65) Prior Publication Data
US 2007/0068528 A1   Mar. 29, 2007

Related U.S. Application Data

(63) Continuation of application No. PCT/EP2005/003181, filed on Mar. 24, 2005.

(30) Foreign Application Priority Data

Mar. 26, 2004 (EP) ..................................... 04007355

(51) Int. Cl.
*A61B 5/085* (2006.01)
*A61M 16/00* (2006.01)
*A61B 5/083* (2006.01)

(52) U.S. Cl.
CPC ............... *A61B 5/085* (2013.01); *A61M 16/00* (2013.01); *A61B 5/0836* (2013.01); *A61M 2016/0021* (2013.01); *A61M 2016/0036* (2013.01); *A61M 2230/202* (2013.01); *A61M 2230/432* (2013.01)

(58) Field of Classification Search
CPC ........... A61M 16/00; A61M 2230/202; A61B 5/085; A61B 5/0836
USPC ............ 128/203.12, 204.18, 204.21, 204.22, 128/204.23, 204.26
See application file for complete search history.

(56) References Cited

U.S. PATENT DOCUMENTS 5,402,796 A *  4/1995  Packer et al. .................. 600/532
5,632,281 A *  5/1997  Rayburn ....................... 600/532
(Continued)

FOREIGN PATENT DOCUMENTS

EP           0745403        4/1996
WO       WO 92/04865       4/1992
(Continued)

OTHER PUBLICATIONS

Tusman et al., "Alveolar Recruitment Strategy Increases Arterial Oxygenation During One Lung Ventilation", 2002, Socienty of Thoracis Surgenons Elseveir Science Inc.*

*Primary Examiner* — Justine Yu
*Assistant Examiner* — LaToya M Louis
(74) *Attorney, Agent, or Firm* — Shlesinger, Arkwright & Garvey LLP

(57) ABSTRACT

Method for providing ventilatory settings with regard to the airway pressure levels of an artificial ventilator, the artificial ventilator is connected to a lung, including the steps of obtaining data samples of a gas concentration of the expired gas over a single breath; selecting a plurality of data samples from the obtained data samples; calculating a tracing value being sensitive to changes of alveolar dead space on the basis of the selected data samples; repeating steps a), b) and c) for obtaining a plurality of tracing values; and changing at least one airway pressure level of the artificial ventilator, wherein from an observation of a resulting course of the plurality of calculated tracing values an airway pressure level at which alveolar opening or lung overdistension or lung open condition or alveolar closing occurs is detected. Apparatus for providing ventilatory settings with regard to the airway pressure levels of an artificial ventilator is also disclosed.

18 Claims, 15 Drawing Sheets

(56) References Cited

U.S. PATENT DOCUMENTS

| | | | | |
|---|---|---|---|---|
| 5,937,854 | A | * | 8/1999 | Stenzler ............... 128/204.23 |
| 6,402,697 | B1 | * | 6/2002 | Calkins et al. ............ 600/532 |
| 6,612,995 | B2 | * | 9/2003 | Leonhardt et al. ......... 600/532 |
| 2002/0193700 | A1 | * | 12/2002 | Bohm et al. .............. 600/533 |
| 2004/0055599 | A1 | * | 3/2004 | Strom .................. 128/204.18 |
| 2004/0097821 | A1 | * | 5/2004 | Blomberg et al. ........... 600/529 |

FOREIGN PATENT DOCUMENTS

| | | |
|---|---|---|
| WO | WO 96/24285 | 8/1996 |
| WO | WO 00/44427 | 8/2000 |

* cited by examiner

NON-INVASIVE METHOD AND APPARATUS FOR OPTIMIZING THE RESPIRATION OF ATELECTATIC LUNGS

FIELD OF THE INVENTION

The invention refers to a method and an apparatus for determining the status of a lung ventilated by an artificial ventilator.

BACKGROUND OF THE INVENTION

Such a method and such an apparatus are known from WO 00/44427 A1. WO 00/44427 A1 deals with the problem of the artificial ventilation of patients with an ailing lung. The basic patho-physiological mechanism of an ailing lung is the lack of surfactant (substance which reduces surface tension) which can cause a collapse of major lung fractions and a dramatically reduced gas exchange area. Hence, to prevent undesirable sequelae and consecutive multiorgan failure, an important goal of protective ventilator therapy is a gentle and early "reopening" of the lung. Through the identification of the alveolar opening and especially of the alveolar closing pressures, a distressed lung may be kept open by proper choice of the airway pressure. However, the manual determination of opening and closing pressures is arduous and time consuming. Therefore, WO 00/44427 A1 suggests to use the partial pressures of oxygen ($paO_2$) as an indicator for determining the opening and closing pressures of the lung. WO 00/44427 A1 has recognized that there is a significant hysteresis behaviour of the $paO_2$ as a function of the ventilation pressure.

FIG. 1 shows the $paO_2$ hysteresis of the same healthy (left) and ailing (right) lung. While there is almost no hysteresis in the healthy lung and the choice of ventilation pressures has no visible impact on the quality of gas exchange, the hysteresis is even more severe in an ailing lung. In many cases, gas exchange may be reduced so strongly that at typical ventilation pressures, a sufficient hemoglobin oxygen saturation (>85 mm Hg) may only be reached if high oxygen concentrations (e.g. 90 . . . 100%) are delivered to the patient.

For such an ailing lung, a ventilation strategy could be to first open the lung with a temporary high inspiratory airway pressure and then ventilate on the descending branch of the hysteresis such that a sufficient tidal volume is reached and gas exchange is maintained. This so called recruitment maneuver has become a common strategy in operating rooms and in the intensive care medicine. In general, to achieve a sufficient tidal volume it is necessary to ventilate the lung with a certain delta pressure, which is defined as:

$$\text{delta pressure} = PIP - PEEP$$

PIP is the peak inspiratory pressure and PEEP is the positive end expiratory pressure. The aim of the recruitment maneuver is to find the alveolar opening pressure and the alveolar closing pressure. It is then possible to set the peak inspiratory pressure slightly higher than the alveolar opening pressure and to set the positive end expiratory pressure slightly higher than the alveolar closing pressure. In this way ideally all previously closed lung units will be re-opened and at the same time all open lung units will be kept open.

During a recruitment maneuver the peak inspiratory pressure is stepwise increased so that as many lung units as possible are re-opened, while at the same time the positive end expiratory pressure is increased in order to keep the newly recruited lung units open. When recruiting a lung, some lung units open up and become overdistended, while other lung units are still closed. Thus, when increasing the peak inspiratory pressure in order to re-open as many lung units as possible, most of the opened lung units will be overdistended.

Due to the hysteresis behaviour of the lung, the values obtained for peak inspiratory pressure and for the positive end expiratory pressure during this process of a stepwise increase are too high to further ventilate the lung once the lung units are opened. Thus they need to be reduced systematically.

At first the excessive peak inspiratory pressure is reduced while the positive end expiratory pressure is maintained at its level. This reduction is performed until an adequate tidal volume is reached. From this point onwards both the peak inspiratory pressure and the positive end expiratory pressure are reduced simultaneously. The aim is to find the lowest value for the positive end expiratory pressure that would just maintain all re-opened lung units open. At this stage the peak inspiratory pressure is a secondary variable of interest. Noticeably, the tidal ventilation will change during this simultaneous reduction of the peak inspiratory pressure and the positive end expiratory pressure, since the relief of overdistension will initially increase the lung's compliance. Once the positive end expiratory pressure is too low to keep all previously re-opened lung units open, the point of alveolar closing is reached.

Having identified the values of the peak inspiratory pressure corresponding to the alveolar opening pressure and the positive end expiratory pressure corresponding to the alveolar closing pressure as outlined above, it is then possible to ventilate the lung in an optimal condition. First, all lung units are re-opened by choosing a peak inspiratory pressure which is slightly higher than the alveolar opening pressure, i.e. 2-5 $cmH_2O$ higher, and choosing a positive end expiratory pressure which is slightly higher than the alveolar closing pressure, i.e. 2-3 $cmH_2O$ higher. Afterwards the peak inspiratory pressure is reduced again to achieve the desired tidal volume. The corresponding ventilation stage corresponds to the optimal condition. An optimal compliance is achieved, since all lung units are opened, and no major overdistension is present.

By way of an example, FIG. 2 shows a typical recruitment maneuver in detail. As shown in FIG. 2, the recruitment maneuver is carried out on the basis of a pressure controlled ventilation. Before the final recruitment maneuver takes place, the alveolar opening pressure and the alveolar closing pressure have to be identified. In a first step (step 1), PIP and PEEP are stepwise increased by means of an incremental limb until the alveolar opening pressures have been detected with regard to PIP and PEEP (steps 2 and 3). The alveolar opening pressure with regard to PIP is usually about 40 $cmH_2O$ in normal lungs and in the range of 55-60 $cmH_2O$ in sick lungs. After a successful alveolar opening, a decremental limb or stepwise decrease of PIP and PEEP is done (step 4) to determine the alveolar closing pressure (step 5). As outlined above initially only PIP is reduced as indicated at the transition from step 3 to step 4 in FIG. 2. After having identified the pressures for alveolar opening and alveolar closing, the final recruitment maneuver (step 6) is done with these new target pressures over 10 breaths and PEEP is set above the alveolar closing pressure to avoid pulmonary re-collapse. For example, PEEP is set 2 $cmH_2O$ above the alveolar closing pressure, i.e.

$$PEEP = PEEP_{close} + 2\ cmH_2O$$

Alternatively, a volume controlled ventilation can be carried out having the advantage that the ventilated volume remains constant and that all changes of the lung status can be related to changes within the alveoli.

In order to avoid the invasive measurement of paO$_2$, WO 00/44427 A1 utilizes according to a first embodiment the endtidal CO$_2$ concentration (etCO$_2$) and/or the CO$_2$ output as feedback signals for identification of the optimal ventilator settings for ailing lungs. Both feedback signals can be measured non-invasively. etCO$_2$ can be obtained by measuring the CO$_2$ concentration at the end of an expiration cycle. CO$_2$ output (unit [ml CO$_2$/min]) can be obtained from continuous measurements of the CO$_2$ concentration (unit [%]) and air flow (unit [ml/min]) and subsequent breathwise computation of $$\dot{V}_{CO_2 Atom} = RR \cdot \int_0^T [CO_2](t) \cdot \dot{V}_{Atom}(t) \mathbb{D} T$$

during one expiration cycle. According to a second embodiment of WO 00/44427 A1, the hemoglobin oxygen saturation (SO$_2$) is measured non-invasively and is used as a feedback signal for identification of optimal ventilation parameters for ailing lungs.

In summary, WO 00/44427 A1 discloses a non-invasive method for determining the alveolar opening or closing of a lung based on one of the measurement of the parameters CO$_2$ concentration (etCO$_2$), CO$_2$ output or hemoglobin oxygen saturation (SO$_2$). However, practical tests have shown various disadvantages of this method. One disadvantage is the fact that a single parameter is subject of various disturbances so that an average value of several parameters has to be taken over several breath cycles which causes a delay in the feed back path. Another disadvantage is the fact that the detection of alveolar opening cannot be clearly distinguished from an overdistension of the lung which could cause severe damages to the lung during the recruitment maneuver.

SUMMARY OF THE INVENTION

Therefore, it is an object of the invention to provide a method and an apparatus for determining the status of a lung ventilated by an artificial ventilator which enables in real time optimal ventilatory settings for a well-conducted recruitment maneuver of an ailing lung.

A method according to the invention for determining the status of a lung ventilated by an artificial ventilator comprises the following steps:
a) obtaining data samples of a gas concentration of the expired gas over a single breath,
b) selecting a plurality of data samples from said obtained data samples,
c) calculating a tracing value being sensitive to changes of alveolar dead space on the basis of said selected data samples,
d) repeating steps a), b) and c) for obtaining a plurality of tracing values, and
e) changing the peak inspiratory pressure and the positive end expiratory pressure of the artificial ventilator, wherein from the observation of the resulting course of the plurality of calculated tracing values the peak inspiratory pressure at which alveolar opening or lung overdistension and/or the positive end expiratory pressure at which lung open condition or alveolar closing occurs are detected.

An apparatus according to the invention for determining the status of a lung ventilated by an artificial ventilator comprises the following features:
a sensor for measuring a gas concentration in the expired gas during a single breath,
an analog to digital converter for obtaining data samples of said gas concentration of the expired gas over a single breath in the time domain,
means for selecting a plurality of data samples from said obtained data samples,
means for calculating a tracing value being sensitive to changes of alveolar dead space on the basis of said selected data samples, and
a data processor which detects during a change of the airway pressure of the artificial ventilator from the resulting course of a plurality of calculated tracing values the peak inspiratory pressure at which alveolar opening or lung overdistension occurs and/or the positive end expiratory pressure at which lung open condition or alveolar closing occurs.

According to a preferred aspect of the invention, the gas concentration represents the CO$_2$ concentration. The CO$_2$ concentration can be obtained using a CO$_2$ single breath test as described below. However, the CO$_2$ single breath test was developed for specific applications and therefore was restricted to evaluate the CO$_2$ concentration over a single breath. In contrast to that, it was found out that other gas concentrations over a single breath could be also used for the purpose of the invention since the invention is based on the hypothesis that a lung recruitment maneuver would reduce alveolar dead space. Starting from this hypothesis, the basic principle of the invention is to derive a tracing value from the gas concentration in the expired gas during a single breath which is sensitive to changes of alveolar dead space. As mentioned above, in the following the CO$_2$ concentration will be used exemplary.

The meaning of alveolar dead space with regard to the CO$_2$ concentration in the expired gas was already studied by R. Fletcher, G. Johnson and J. Brew in: "The Concept of Deadspace with Special Reference to Single Breath Test for Carbon Dioxide." Br. J. Anaesth., 53, 77, 1981 and will be explained further below with regard to FIG. 3.

FIG. 3 shows a plot of expiratory gas CO$_2$ concentration against expired volume, which can be obtained by combining a CO$_2$ concentration measurement against time and a volume rate measurement against time. This plot is called the CO$_2$ single breath test and shows three distinct phases in breath CO$_2$ gas concentration during the patient exhale cycle. Phase I represents CO$_2$ free gas expired from the airway conduction structures where gas exchange does not occur. Phase II is characterized by an S-shaped upswing and represents the transition from airway to alveolar gas. Phase III reflects the exhalation of unmixed gas from regions of the lung which normally are in active exchange with the alveolar tissue and thus closely resembles at least in healthy patients gas properties associated with arterial blood in contact with the lung for gas exchange, i.e. CO$_2$ release and O$_2$ absorption. In normal lungs, Phase III is characterized by a horizontal level since ventilated and perfused alveolar regions are closely matched. In a diseased lung, Phase III may not appear horizontal due to a mismatch in ventilation and perfusion of this lung region.

The variables of the graph according to FIG. 3 have the following meaning:
paCO2 is the partial pressure of carbon dioxide.
etCO2 is the endtidal CO2 concentration of a single breath.
X is the alveolar tidal volume and represents true alveolar gas which is the result of a gas exchange in the alveoli.
Y is the alveolar deadspace which is that part of inspired gas which reaches the alveoli but does not take part in gas exchange.

Z is the airway deadspace which is that part of inspired gas which does not reach the alveoli and therefore does not take part in gas exchange either.

The plot according to FIG. 3 is formed by the exhaled partial pressure of $CO_2$ against the expiratory tidal volume. Its analysis can be performed, e.g., using a side-stream infrared capnometer and a pneumotachograph of the Capnomac Ultima (e.g. Datex-Engstrom Instrument, Corp., Helsinki, Finland) or a main-stream $CO_2$ sensor (e.g. Novametrix, USA). Furthermore, a computer is provided to record and analyze data.

Before anesthesia and ventilating a patient, capnograph and blood gas analyzer should be calibrated using the same $CO_2$ concentration (5%). Airway flow can be measured and integrated to obtain volume. A corresponding device automatically normalizes airway volumes from standard condition to body temperature, ambient pressure and water vapor saturation (BTPS). Before anesthesia and ventilating a patient, induction the volume calibration can be done with e.g. a 700 ml super-syringe following the manufacturer's guidelines.

The side-stream $CO_2$ signal has a time delay with respect to the flow signal. A corresponding software can correct the $CO_2$ delays automatically using mathematical algorithms. The $VTCO_{2,br}$ or area under the curve can be computed by integrating expired flow and $CO_2$ in each breath. Analysis of dead space can be done on-line and/or off-line using Fowler's analysis and adding arterial $PCO_2$ values to the $CO_2$ curve of the single breath test.

A well known application of the $CO_2$ single breath test is the so called capnography, which is a technique to assess the arterial carbon dioxide content, expressed as partial pressure of $CO_2$ ($paCO_2$), and which is disclosed in detail in WO 92/04865 A1 and WO 96/24285 A1. Since alveolar dead space cannot be derived directly from the $CO_2$ single breath test, both WO 92/04865 A1 and WO 96/24285 A1 assume alveolar dead space as a constant variable which has to be determined or estimated by other means, e.g. by a separate blood sample. Hence, according to WO 92/04865 A1 and WO 96/24285 A1 any changes of alveolar dead space are seen as a disturbance variable, since these changes result in a faulty estimate of $paCO_2$.

In contrast to that the invention takes a new course for evaluating the $CO_2$ single breath test, since the invention uses now a tracing value which is sensitive to changes of alveolar dead space in order to determine certain lung conditions, namely alveolar opening or lung overdistension or lung open condition or alveolar closing. Hence, changes of alveolar dead space are no longer seen as a disturbance variable but are now taken as an indicator for certain lung conditions.

Since the meaning of alveolar dead space despite the well investigated single breath test with regard to the detection of alveolar opening or lung overdistension or lung open condition or alveolar closing of a ventilated lung was not recognized so far, the physiologic concept for alveolar dead space will be explained further below.

FIG. 4 shows the anatomical and functional units of the lungs, namely the lung acinus. The meaning of the abbreviations is as follows:
  Cap=pulmonary capillary
  alv=alveolus
  Calv=alveolar duct
  Salv=alveolar sac
  RB=respiratory bronchiole.

The lung acinus is constituted of the respiratory bronchioli, alveolar ducts, alveolar sacs, alveoli and pulmonary capillaries. To maintain a normal function, this acinus must be well-ventilated and perfused, i.e must be maintained in an open condition. If this acinus becomes collapsed, it loses its normal capacity for gas exchange and makes itself prone to injury during artificial ventilation, as stated previously.

Diffusion is a process fundamental to life because it is responsible for blood oxygenation and $CO_2$ removal within the lungs. FIG. 5 shows the diffusion phenomenon for $CO_2$ which is defined as a passive movement of $CO_2$ molecules through the alveolar-capillary membrane due to a gradient of concentration or partial pressures.

Diffusion is studied by Fick's law:

$$J = Dmol\, A\, Dc/Dx$$

where J is the instantaneous flux of $CO_2$, Dmol represents the gas-phase molecular diffusivity of $CO_2$ in air, A is the area of gas exchange, and Dc the gas concentration gradient for $CO_2$ and Dx is the distance.

During normal physiology and in most of the pathological states, Dmol, Dc, and Dx remain roughly constant. This means that the area (A) becomes the main factor responsible for changes in the diffusion process within the lung.

The area of gas exchange depends on a normal acinar structure. Reduction in A is the consequence of pathologic three-dimensional changes in acinar morphology. Thus, a decrease in A as during lung collapse results in a decrease of the $CO_2$ and $O_2$ diffusion at the alveolar-capillary membrane. Opposite to that, the recovery of a normal acinar morphology by a recruitment maneuver normalizes A and thus diffusion.

According to the invention, the three-dimensional structural changes of the lung acini are reflected in a change of alveolar dead space during a $CO_2$ single breath test, wherein a suitable tracing value is used to detect these changes. The tracing value represents a data fusion of the data samples of the $CO_2$ concentration using an average data algorithm. Examples of average data algorithms are a least squares linear regression, a weighted sum calculation or a FIR (finite impulse response) filter.

In contrast to WO 00/44427 A1 the method and the apparatus according to the invention has the advantage that an averaged value within one single breath is obtained which still yields a good accuracy for determining certain lung conditions. An important cognition of the invention compared to WO 00/44427 A1 is the fact that a plurality of data samples from said obtained data samples are selected which enables a selective evaluation of the $CO_2$ concentration within one single breath.

According to a preferred aspect of the invention, the data samples according to step a) are obtained in the time domain. This can be achieved by a conventional analog to digital converter. According to another preferred aspect of the invention, the obtained data samples are converted from the time domain into the volumetric domain. This is particularly useful for obtaining the well known plot of the $CO_2$ single breath test.

FIG. 6 shows some possible tracing values within a plot of a $CO_2$ single breath test, which are

| | |
|---|---|
| slope III or endtidal mean slope | determined by the mean slope (either over time or over volume) of the $CO_2$ concentration in the expired gas towards the final stage of a single breath, |
| slope II or steepest mean slope | determined by the steepest mean slope (either over time or over volume) of the $CO_2$ concentration in the expired |

| | |
|---|---|
| angle II-III | gas in vicinity of the point of inflection, determined by the angle between slope II and slope III, |
| intercept II | determined by the intersecting point of slope II with the X-axis, and |
| intercept III | determined by the intersecting point of slope III with the Y-axis. |

The following table shows an overview of these and some more tracing values together with their sensibility with regard to the lung stages "recruitment", "overdistension", "open-lung" and "re-collapse":

| Variable | recruitment | overdistension | open-lung | Re-collapse |
|---|---|---|---|---|
| $VD^{aw}$ | ↑↑ (+++) | ↑↑↑ (+++) | ↓↓ (+) | ↓↓ (+) |
| $VD^{aw}/VT$ | ↑↑ (+++) | ↑↑↑ (+++) | ↓↓ (+) | =↓ (+) |
| VCO2 | ↑↑ (+++) | ↓↓ (+++) | ↑ (+) | =↓ (+) |
| $P_{AE}CO2$ | ↑↑ (+++) | ↓↓ (+++) | ↑ (+) | =↓ (+) |
| etCO2 | ↑↑ (+) | =↓ (−) | =↓ (−) | ↓ (−) |
| $VTCO2_{,br}$ | ↑↑ (+++) | ↓↓ (+++) | ↑↑ (+) | =↓ (+) |
| $VT^{alv}$ | ↓ (+) | ↓ (−) | ↑ (−) | = (+) |
| Angle II-III | ↓↓↓ (+++) | ↑↑↑ (+++) | ↓↓ (+) | ↑↑↑ (+++) |
| Slope II | ↑↑↑ (+++) | ↓↓ (+) | ↑↑ (+) | ↓↓ (+) |
| Slope III | ↓↓↓ (+++) | ↑ (−) | ↓ (+) | ↑↑ (+++) |
| Vol I | ↑↑↑ (+++) | ↑ (−) | ↓ (+) | ↓ (+) |
| Vol II | ↑↑ (+++) | ↑ (+) | ↓↓ (+) | =↑ (++) |
| Vol III | ↓↓↓ (++) | ↓ (+) | ↑↑ (+) | =↓ (+) |
| Intercept II | ↓↓↓ (+++) | =↓ (−) | ↑ (+) | =↑ (++) |
| Intercept III | ↑↑↑ (+++) | ↓ (+) | ↑ (+) | =↑ (−) | with:
=: no change
1 arrow: small change
2 arrows: moderate change
3 arrows: large change
(−): no sensivity
(+): low sensivity
(++): moderate sensivity
(+++): high sensivity.

The meaning of the variables with regard to their use as tracing values is as follows:

$VD^{aw}$: airway dead space. Is the dead space created by the convective airways to the point where mixing with alveolar gas takes place (FIG. 3, Z area). The midpoint of phase II is the limit between anatomical dead space and alveolar gas (Fowler's method). This midpoint is calculated as 50% of numerical data from slope II. It represents the gas inside the lung transported by convection.

$VCO_2$: is the production of $CO_2$ per minute (ml/min) and is calculated as the product of the expired concentration of $CO_2$ by the alveolar minute ventilation.

$VTCO_{2,br}$: or area under the curve, it represents the volume of $CO_2$ expired in a single breath measured by flow integration (FIG. 3, X area). It is useful to calculate $CO_2$ production. It represents the alveolar gas, which is in contact with pulmonary capillary blood.

Phase I: begins with the start of expiration (detection by a negative inflection on flow signal), and ends when the concentration of $CO_2$ in the $CO_2$ single breath test increases above 0.1% from baseline (FIG. 3, FIG. 6).

Phase II: starts at the end of phase I (from 0.1% $CO_2$ concentration) and continues to the intersection of the predictive slope lines for phases II and III (FIG. 3, FIG. 6).

Phase III: or alveolar plateau begins at the intersection of the predictive slopes lines for phase II and III and terminates at the end of expiration, defined by an abrupt positive deflection on flow signal (FIG. 3, FIG. 6).

Volume of phase I: Is the volume of gas contained in the phase I. It determines the largest part of the airway dead space and represents the gas in the proximal airway and the compressive gas in the ventilatory circuit (FIG. 3, FIG. 6).

Volume of phase II: Is the volume of gas contained in the phase II: The midpoint of phase II (50% of slope) is the limit between anatomical dead space and alveolar gas, and represents an interface when convective gas transport changes to diffusion transport in lung acini. Thus, phase II is part of both, airway dead space and alveolar gas Phase II is highly influenced by the acinar emptying time: the more homogeneous the gas emptying for the acini the lower is the phase II volume (FIG. 3, FIG. 6).

Volume of phase III: This volume represents the gas inside the alveoli in contact with pulmonary capillary blood. It is considered as efficient volume for gas exchange within the tidal volume (FIG. 3, FIG. 6).

Slope of phase II: It is derived i.e. from least squares linear regression using data points collected between 25-75% of the phase II, expressed as fraction (FIG. 6). The phase II slope of individual breaths is normalized by dividing the slope value by the corresponding mean alveolar fraction of $CO_2$ or $PAECO_2$ (expressed in %). Similar to volume of phase II, the slope represents the spread of acinar expiratory times. If all acini were emptying at almost the same time the ventilation would be more homogeneous and the slope increases. An opposite change in slope II represents an inhomogeneous gas emptying as observed i.e during atelectasis (lung collapse) (FIG. 6).

Slope of phase III: It is derived from e.g. least squares linear regression using data points collected between 25-75% of the phase III, expressed as fraction (FIG. 6). The phase III slope of individual breaths is normalized by dividing the slope value by the corresponding mean alveolar fraction of $CO_2$ or $PAECO_2$ (expressed in %). Phase III slope is the most useful variable to measure a recruitment effect. It is related to the ventilation/perfusion relationship (V/Q): when the V/Q ratio is more efficient the phase III slope decreases, representing a decrease in $CO_2$ diffusional resistance. When slope III increases, a V/Q mismatch is found.

Mathematical models have described the variables that can change phase III slope. They are: tidal volume, respiratory rate (only in the extreme of normal values), area of gas exchange, and gas diffusivity. Maintaining all variables stable that can change phase III slope, any change in the area of gas exchange can thus affect this slope. Fick's first law of diffusion can easily explain this statement.

Angle II-III: It is defined as the angle of intersection between slope of phase II and III. Changes in this angle represent changes of the shape of the $CO_2$ single breath test related to the efficiency/inefficiency state of ventilation and gas exchange. When the angle decreases, as after lung recruitment, ventilation and gas exchange improve. Increasing angles II-III are related to an inhomogeneous (and worse) ventilation/perfusion relationship (FIG. 6).

Intercept of phase II slope: It is defined as the intersection of the line of phase II slope with the X axis (FIG. 6).

Intercept of phase III slope: It is defined as the intersection of the line of phase III slope with the Y axis (FIG. 6).

$VT^{alv}$: It represents the portion of tidal volume that is located distal to the interface, it is true alveolar gas. This volume is constituted by the sum of $VTCO_2^{alv}$ plus $VD^{alv}$. $VT^{alv}$ is derived by Fowler analysis as $VT-VD^{alv}$.

$PAECO_2$: or mean expired concentration of $CO_2$, constitutes the mean partial pressure of $CO_2$ in alveolar air. It is defined as the partial pressure of $CO_2$ at the middle of the slope III. This value represents the partial pressure of all $CO_2$ molecules in the expired volume.

$etCO_2$: is the end tidal partial pressure of $CO_2$ (FIG. 3).

$Pet-AECO_2$: is the difference between end tidal $CO_2$ and mean expired partial pressure. It is an index of alveolar dead space: the higher the differences between these two values, the higher is the inefficiency of lung function.

VDBohr: is the dead space formed by anatomical dead space plus part of the alveolar dead space (ml), defined as the lower portion of the alveolar dead space.

Vdaw/VT: the ratio between airway dead space to tidal volume, is an index of lung efficiency/inefficiency. The higher this index is the more inefficient the lung becomes.

It should be noted that Volume I, II, III and phase III slope are normalized by dividing them by the tidal volume to make comparison among different breaths possible.

According to a preferred aspect of the invention the endtidal mean slope is taken as a tracing value and is determined by the mean slope (either over time or over volume) of the $CO_2$ concentration in the expired gas towards the final stage of a single breath. The calculation of the endtidal mean slope can be carried out on the basis of a least squares linear regression using suitable constraints, wherein a suitable constraint could be a minimum mean square error of the regression result over a predetermined range. On the basis of such a constraint the calculation of the endtidal mean slope would be carried out as follows:

Step 1: Performing on the basis of the data points of the measured $CO_2$ concentration of a single breath a running least squares linear regression over a predetermined range (either with regard to volume or time), wherein the predetermined range is a certain percentage of the expired volume or of the respiratory period, e.g. 20%.

Step 2: Identifying the range for which the mean square error of the running least squares linear regression becomes a minimum towards the final stage of a single breath.

Step 3: Setting the slope of the least squares linear regression over the identified range of step 2 as the tracing value of said single breath.

According to a preferred aspect of the invention, the peak inspiratory pressure of the artificial ventilator is increased stepwise breath by breath starting from alveolar closing, wherein an alveolar opening of the lung is detected, if the resulting course of the plurality of determined first tracing values reaches a minimum.

According to another preferred aspect of the invention, the peak inspiratory pressure of the artificial ventilator is increased stepwise breath by breath starting from alveolar opening, wherein a lung overdistension is detected, if the positive gradient of the resulting course of the plurality of determined first tracing values reaches a maximum.

According to another preferred aspect of the invention, the positive end expiratory pressure of the artificial ventilator is decreased stepwise breath by breath starting from lung overdistension, wherein an open lung condition is detected, if the resulting course of the plurality of determined first tracing values reaches a minimum.

According to another preferred aspect of the invention, the positive end expiratory pressure of the artificial ventilator is decreased stepwise breath by breath starting from an open lung condition, wherein an alveolar closing is detected, if the positive gradient of the resulting course of the plurality of determined first tracing values reaches a maximum.

According to another preferred aspect of the invention a second tracing value is represented by the steepest mean slope of the $CO_2$ concentration in the expired gas during a single breath. The steepest mean slope is determined by the mean slope (either over time or over volume) of the $CO_2$ concentration in the expired gas in the vicinity of the point of inflection. The calculation of the steepest mean slope can be carried out again on the basis of a least squares linear regression using suitable constraints, wherein a suitable constraint could be a minimum mean square error of the regression result over a predetermined range. On the basis of such a constraint the calculation of the steepest mean slope would be carried out as follows:

Step 1: Performing on the basis of the data points of the measured $CO_2$ concentration of a single breath a running least squares linear regression over a predetermined range (either with regard to volume or time), wherein the predetermined range is a certain percentage of the expired volume or of the respiratory period, e.g. 20%.

Step 2: Identifying the range for which the mean square error of the running least squares linear regression becomes a minimum in the vicinity of the point of inflection.

Step 3: Setting the slope of the least squares linear regression over the identified range of step 2 as the tracing value of said single breath.

According to another preferred aspect of the invention, the peak inspiratory pressure of the artificial ventilator is increased stepwise breath by breath starting from alveolar closing, wherein an alveolar opening of the lung is detected, if the resulting course of the plurality of determined second tracing values reaches a maximum.

According to another preferred aspect of the invention, the peak inspiratory pressure of the artificial ventilator is increased stepwise breath by breath starting from alveolar opening, wherein a lung overdistension is detected, if the negative gradient of the resulting course of the plurality of determined second tracing values reaches a minimum.

According to another preferred aspect of the invention, the positive end expiratory pressure of the artificial ventilator is decreased stepwise breath by breath starting from lung overdistension, wherein an open lung condition is detected, if the resulting course of the plurality of determined second tracing values reaches a maximum.

According to another preferred aspect of the invention, the positive end expiratory pressure of the artificial ventilator is decreased stepwise breath by breath starting from an open lung condition, wherein an alveolar closing is detected, if the negative gradient of the resulting course of the plurality of determined second tracing values reaches a minimum.

According to another preferred aspect of the invention a third tracing value is represented by the angle between the endtidal mean slope and the steepest mean slope of the $CO_2$ concentration in the expired gas during a single breath.

According to another preferred aspect of the invention, the peak inspiratory pressure of the artificial ventilator is increased stepwise breath by breath starting from alveolar closing, wherein an alveolar opening of the lung is detected, if the resulting course of the plurality of determined third tracing values reaches a minimum.

According to another preferred aspect of the invention, the peak inspiratory pressure of the artificial ventilator is increased stepwise breath by breath starting from alveolar opening, wherein a lung overdistension is detected, if the positive gradient of the resulting course of the plurality of determined third tracing values reaches a maximum.

According to another preferred aspect of the invention, the positive end expiratory pressure of the artificial ventilator is decreased stepwise breath by breath starting from lung overdistension, wherein an open lung condition is detected, if the resulting course of the plurality of determined third tracing values reaches a minimum.

According to another preferred aspect of the invention, the positive end expiratory pressure of the artificial ventilator is decreased stepwise breath by breath starting from an open lung condition, wherein an alveolar closing is detected, if the positive gradient of the resulting course of the plurality of determined third tracing values reaches a maximum.

According to another preferred aspect of the invention, a plurality of different types of tracing values are calculated in parallel and wherein from the resulting course of the plurality of different types of tracing values the peak inspiratory pressure at which alveolar opening or lung overdistension and/or the positive end expiratory pressure at which lung open condition or alveolar closing occurs are detected.

According to another preferred aspect of the invention, during a recruitment maneuver of the lung the peak inspiratory pressure is set above the peak inspiratory pressure at which alveolar opening has been detected and the positive end-expiratory pressure is set above the positive end expiratory pressure at which alveolar closing has been detected.

Other objects and features of the invention will become apparent by reference to the following specification and to the drawings in which FIG. 1 to FIG. 6 have been referred to already in the introductory part of the description and in which FIG. 7 to FIG. 12 will be explained now in further detail.

DETAILED DESCRIPTION OF THE INVENTION

Figure 7:
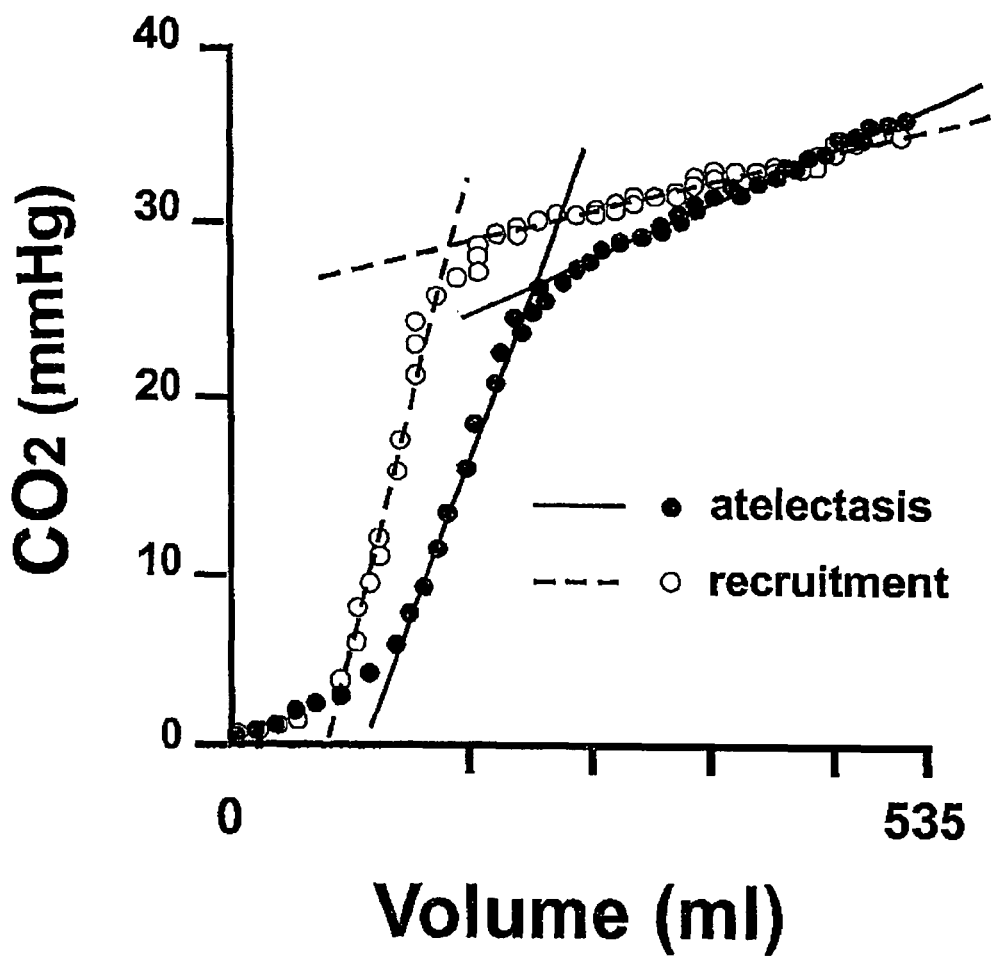
FIG. 7 shows two plots of a $CO_2$ single breath test in the states of atelectasis and recruitment.

FIG. 7 shows two plots of a $CO_2$ single breath test in the states of atelectasis and recruitment. As it can be seen, an increase in the area of gas exchange due to recruitment alters the shape of the plot of a $CO_2$ single breath test, wherein the endtidal mean slope (slope III) decreases and the steepest mean slope (slope II) increases. Hence, taking into account the above theoretical explanation, the reversible and dynamic acinar change in morphology can be manipulated by treatment. Normalizing acinar morphology in a mechanically ventilated patient by a recruitment maneuver produces a normalisation in the physiology of the lung. A normalisation in acinar morphology by the recruitment maneuver causes an improvement in gas exchange and in gas emptying during expiration.

Figure 8:
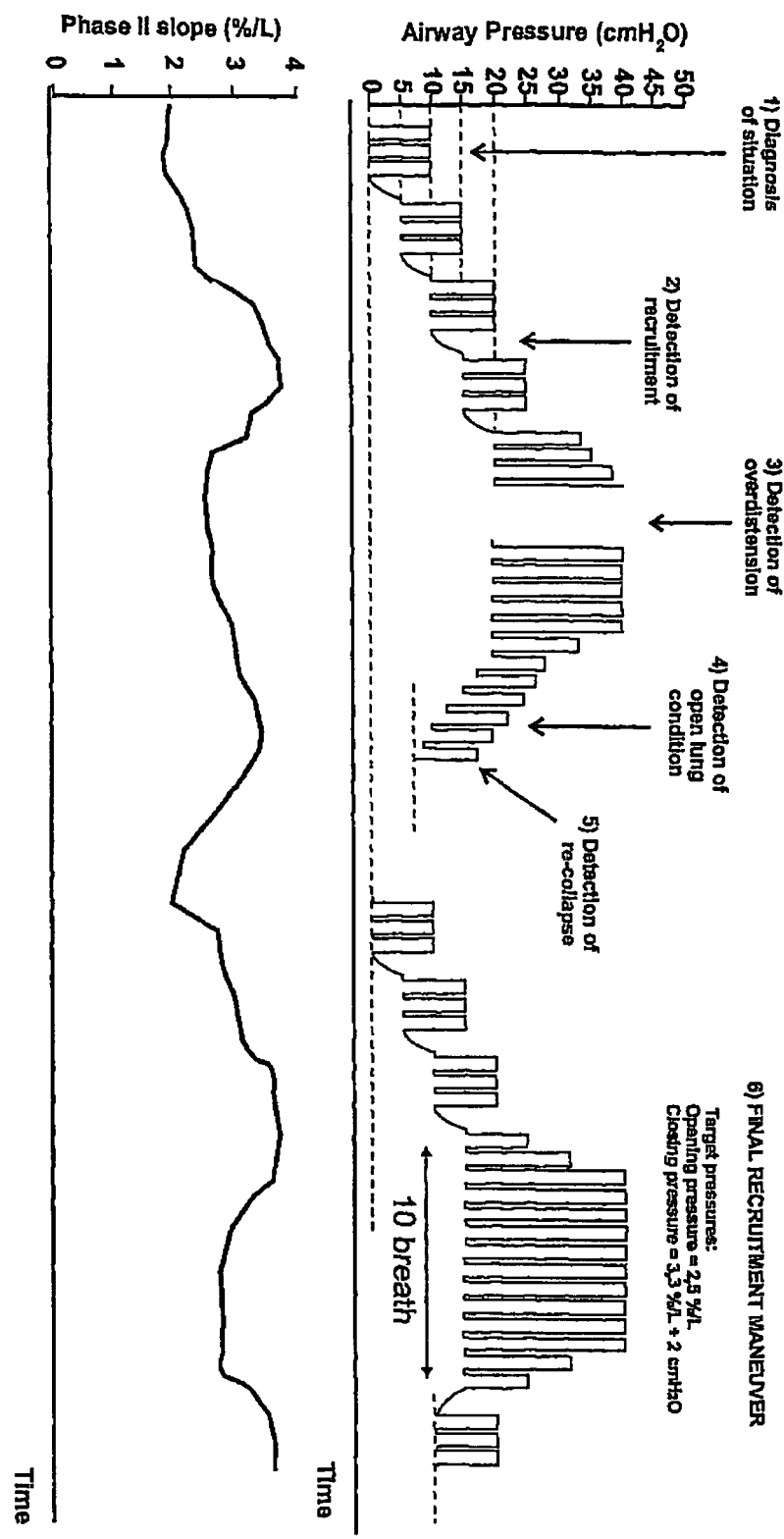
FIG. 8 shows a plot of the airway pressures over time of a typical recruitment maneuver together with the response of the steepest mean slope as a tracing value.

FIG. 8 shows a plot of the airway pressures over time of a typical recruitment maneuver together with the response of the steepest mean slope (slope II) as a tracing value. The algorithm for diagnosing the lung's open-collapse state is described with regard to the steepest mean slope as follows:

1. Analysis of the Baseline Situation

An analysis of the $CO_2$ single breath test is performed before the recruitment maneuver. This data are considered as the control values for comparison with values observed during and after the recruitment maneuver.

2. Analysis of Lung Recruitment

During the recruitment maneuver the behavior of the steepest mean slope in each breath is observed and typical recruitment effects are detected.

3. Analysis of Lung-Overdistension

At the end of the incremental limb of the recruitment maneuver the behavior of the steepest mean slope in each breath is observed and typical overdistension effects are detected.

4. Analysis of the Open-Lung Condition

During the decreasing limb of the recruitment maneuver the steepest mean slope is analyzed in every breath searching for changes representing the open-lung condition.

5. Analysis of the Lung Re-Collapse

During the decreasing limb of the recruitment maneuver the steepest mean slope is analyzed in every breath searching for changes representing lung re-collapse.

6. Final Recruitment Maneuver

A new recruitment maneuver is done with the known opening and closing pressure.

Although the algorithm merely has been described with s regard to the steepest mean slope as a tracing value, it goes without saying that any other suitable tracing values as listed above or combinations thereof can be taken as a basis for carrying out the algorithm.

Figure 9:
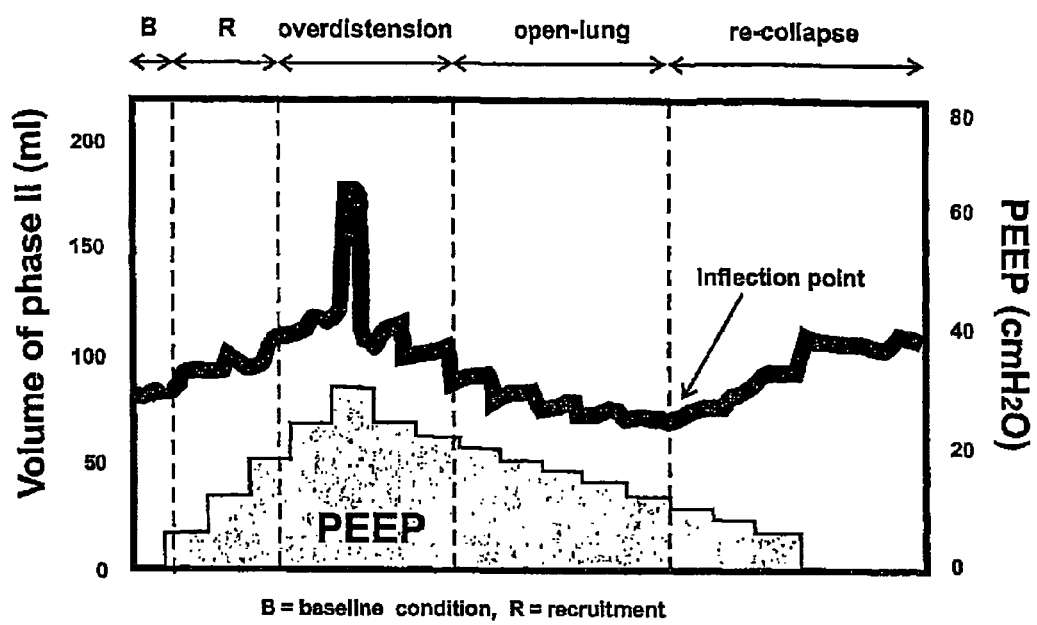
FIG. 9 shows a plot of the airway pressures over time of a typical recruitment maneuver together with the response of the volume of phase II as a tracing value.

FIG. 9 shows a plot of the airway pressures over time of a typical recruitment maneuver together with the response of the volume of phase II as a tracing value. Lung recruitment, overdistension, open-lung condition and re-collapse are seen during the recruitment maneuver. The is inflection point represents the change of direction of the volume of phase II from the open-lung condition to the beginning of the collapsed state. Furthermore, the inflection point represents the pulmonary closing pressure.

In the following, a first study concerning the effect of an alveolar recruitment strategy (ARS) on gas exchange and lung efficiency during one-lung ventilation (OLV) is discussed using the single breath test of $CO_2$.

A total of 12 patients were studied during general anesthesia for elective open thoracic surgery or thoracoscopy. Patients with acute or chronic uncompensated cardiopulmonary disease were not included in the study.

Only for open thoracotomies, a thoracic epidural catheter was placed at T2 to T4 and a total volume of 0.1 ml/kg of bupivacaine 0.5% without epinephrine were administered. Prior to the epidural anesthesia, intravascular volume was expanded by infusing 7 ml/kg of a colloidal solution (Haemacell™) and maintained at 8 ml kg$^{-1}$ h$^{-1}$ of normal saline solution.

After 3 minutes of breathing 100% oxygen, general anesthesia was induced with fentanyl 5 µg/kg, thiopental 3 mg/kg and vecuronium 0.08 mg/kg iv. Anesthesia was maintained with isofluorane 0.5-0.6 MAC and epidural lidocaine 1% boluses of 5 ml for open thoracotomies. For thoracoscopies and minimal invasive coronary artery by-pass graft (mini-CABG), anesthesia was maintained with isofluorane 0.7-1 MAC and boluses of fentanyl 2 ug/kg and vecuronium 0,015 mg/kg as clinically necessary. The trachea and the left bronchus were intubated with a left double lumen tube (DLT) of the appropriate size (Broncho-Cath™, Mallinckrodt Laboratories, Atholone, Ireland). Air leakage were assessed by introducing the capnograph's side stream sensor into each lumen of the DLT while maintaining ventilation through the other lumen. Bronchoscopy confirmed the correct position of the DLT before and after positioning the patients in the lateral position. During OLV, the lumen of the non-ventilated side was left open to atmosphere.

Lungs were ventilated with a Servo 900 C in a volume control ventilation mode and an inspired oxygen fraction ($FiO_2$) of 1.0. The ventilator delivered a square-wave flow with an inspiratory time of 33% with no end-inspiratory pause. The respiratory rate was set between 10-14 breathe/min, tidal volumes (VT) were maintained at 8 ml/kg, and PEEP was 8 cmH$_2$O throughout the study.

During OLV, tidal volume was reduced to 6 ml/kg to avoid peak pressures higher than 30 cmH$_2$O. Respiratory rate was increased to 15-18 breaths/min to maintain the same minute ventilation as during TLV.

Standard monitoring was performed with the Cardiocap II monitor. A Capnomac Ultima monitor was used to measure the following ventilation parameters and gas concentrations: Peak inspiratory pressure (PIP), PEEP, expired tidal volume (VTe), respiratory rate, expired minute volume, $O_2$ and $CO_2$ fractions.

Carbon dioxide elimination ($VCO_2$) was calculated as the product of alveolar ventilation times the mean expired alveolar fraction of $CO_2$ ($FAECO_2$%). Oxygen consumption ($VO_2$) was calculated as the product of alveolar ventilation times the inspiratory-expiratory $O_2$ difference. Respiratory quotient (RQ) was calculated dividing $VCO_2$ by $VO_2$. The single breath analysis for $CO_2$ was performed using the sidestream infrared capnometer and the pneumotachograph of the Capnomac Ultima and a signal processor. Data were recorded and analyzed by a computer.

Capnograph and blood gas analyzer were calibrated using a known gas concentration of $CO_2$ (5%). This calibration was performed in each patient before the induction of anesthesia. Airway flow and pressure measurements are based on the measurement of kinetic gas pressure, and are performed using the Pitot effect. Flow rate is measured and integrated to obtain VT. The Capnomac device restores normal airway volumes from standard condition to body temperature, ambient pressure and water vapor saturation (BTPS) automatically. Volume calibration was done with a 700 ml super-syringe before anesthesia induction following the manufacturer's guidelines.

The sidestream $CO_2$ signal has a time delay compared to the flow signal. The software automatically corrected the $CO_2$ delay using commonly known mathematical algorithms. The $VTCO_{2,br}$ or area under the curve was computed by integrating expired flow and $FCO_2$ in each breath.

Figure 3:
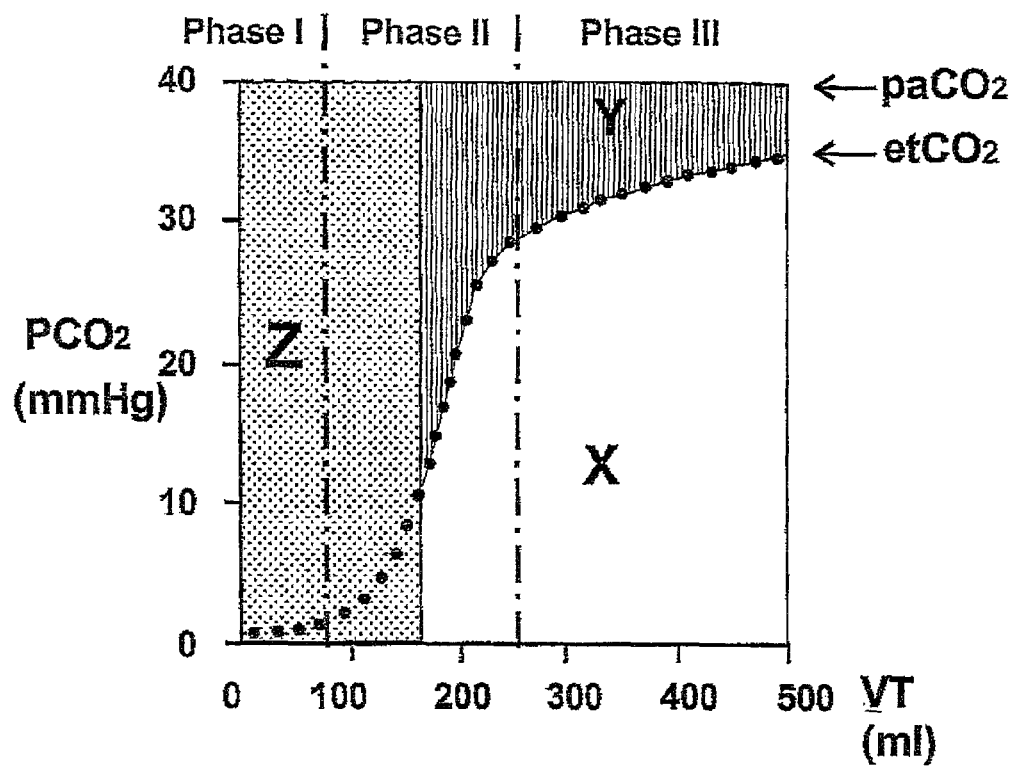
FIG. 3 shows a plot of the $CO_2$ single breath test with three distinct phases in breath $CO_2$ gas concentration during the patient exhale cycle.
Figure 4:
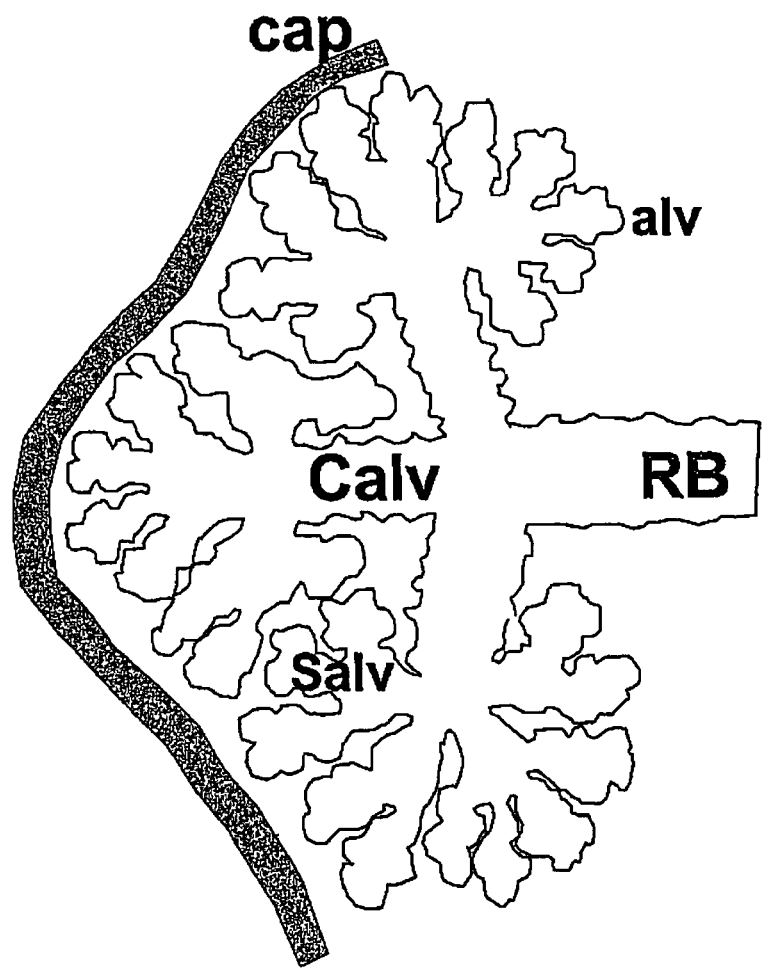
FIG. 4 shows a schematic diagram of the anatomical and functional units of the lungs.
Figure 5:
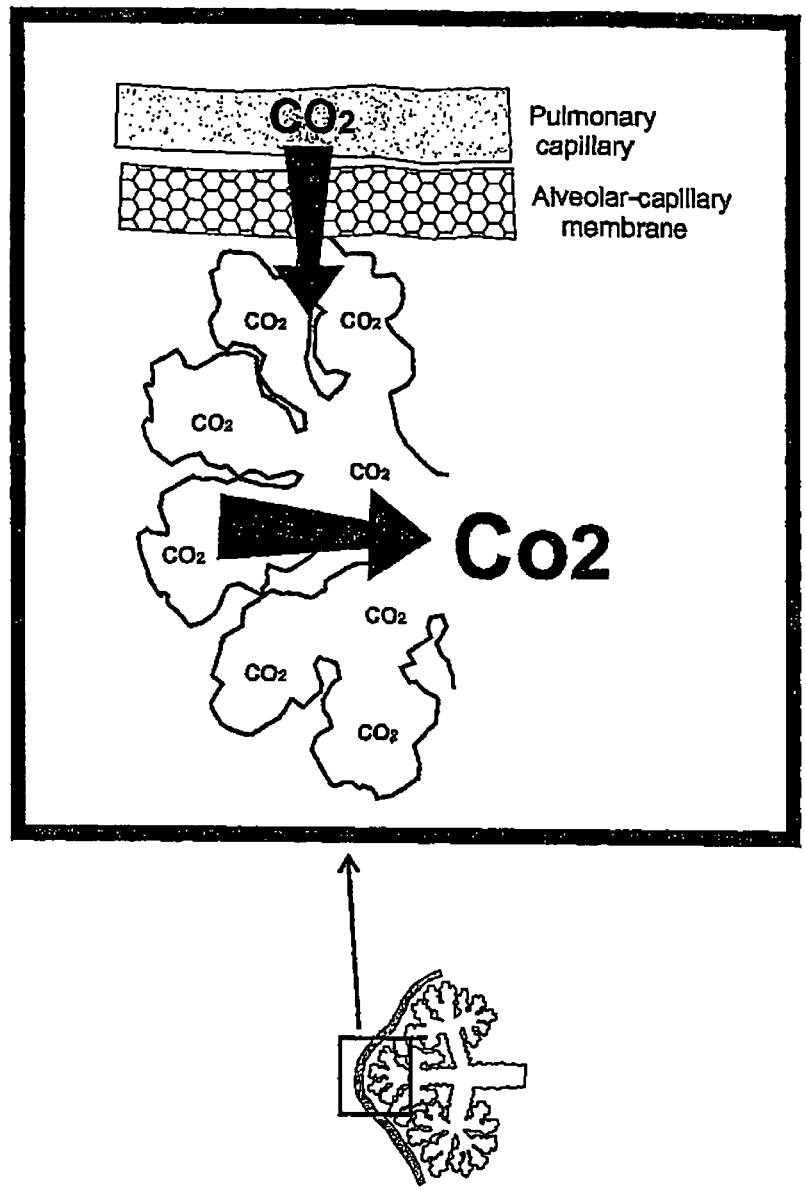
FIG. 5 shows a schematic diagram of the diffusion phenomenon for $CO_2$ in a human's lung.

Analysis of dead space was done off-line using Fowler's analysis and adding $PaCO_2$ value to the $CO_2$ curve of the single breath test (FIG. 3). The mean value of 3 consecutive $CO_2$ single breath tests was used for each variable. The dead space of the apparatus was 60 ml (10 ml from D-LITE™ plus 50 ml from DLT connections) and was subtracted from the airway dead space value.

All measurements were performed with the patient in the lateral position. Arterial blood gases, $CO_2$ single breath test data, ventilatory and hemodynamic data were recorded at three points:

a) TLV: 15 minutes after placing the patient in the lateral position with the chest still closed.

b) $OLV_{PRE}$: after 20 minutes of OLV ventilation, before applying the ARS.

c) $OLV_{ARS}$: 20 minutes after applying the ARS selectively to the dependent lung.

Patients were studied during OLV prior to any vascular interruption in the non-dependent lung. During OLV patients were studied at the moment of highest shunt prior to any vascular clipping in the nondependent lung.

The recruitment maneuver was applied selectively to the dependent lung immediately after the measurement at point b. First, the ventilator was switched to pressure control ventilation, adjusting the level of pressure to obtain the same tidal volume as during volume control ventilation. Ventilation was then allowed to equilibrate for three minutes. Thereafter, the ARS was performed based on an established concept. The critical alveolar opening pressure was assumed to be at 40 cmH$_2$O as described for healthy lungs.

Comparison of variables between points was carried out using repeated-measure analysis of variance. If the analysis of the variance F-statistic was significant the Student-Newman-Keuls post-test detected significant differences. Values are reported as mean±SD and a p<0.5 was considered significant.

Twelve patients, 10 men and 2 women, were included in this study. The following table shows the patients data. Only patient number 7 received inhaled bronchodilators sporadically as needed.

| P | Age (yrs) | Gender | BMI (Kg/h$^2$) | FEV$_1$ (Lts/%) | pH | PaO$_2$ (mmHg) | PaCO$_2$ (mmHg) | Smoking (p/Year) | Surgery |
|---|---|---|---|---|---|---|---|---|---|
| 1 | 71 | M | 26 | 2.1/84 | 7.39 | 64 | 36 | 50 | RUL |
| 2 | 48 | M | 28 | 3.0/93 | 7.43 | 101 | 39 | NO | RUL |
| 3 | 57 | F | 24 | 2.4/101 | 7.43 | 91 | 40 | NO | RML |
| 4 | 65 | M | 23 | — | 7.40 | 84 | 44 | NO | Thoracoscopy |
| 5 | 66 | M | 29 | 2.5/85 | 7.36 | 95 | 39 | 30 | Mini-CABG |
| 6 | 72 | F | 23 | 1.8/73 | 7.44 | 81 | 39 | 25 | Mini-CABG |
| 7 | 73 | M | 26 | 1.7/67 | 7.50 | 73 | 38 | 41 | LUL |
| 8 | 73 | M | 27 | 1.9/78 | 7.35 | 84 | 42 | 22 | Thoracoscopy |
| 9 | 19 | M | 23 | — | 7.44 | 99 | 37 | NO | Thoracoscopy |
| 10 | 58 | M | 30 | 2.9/89 | 7.34 | 89 | 43 | NO | RLL |
| 11 | 74 | M | 28 | 2.2/79 | 7.48 | 75 | 41 | 45 | RUL/RML |
| 12 | 66 | M | 27 | 2.6/96 | 7.34 | 83 | 39 | NO | Mini-CABG |
| Mean | 62 | | 26 | | 7.41 | 85 | 40 | | |
| SD | 15 | | 2.4 | | 0.06 | 11 | 2.3 | | |

Age (years), BMI = body mass index (kg m$^{-2}$)
FEV$_1$ (absolute values in liters and % of normal values), smoking history measured in total pack-year (N° cigarettes smoked per day/20 × N° years of smoking). PaO$_2$, PaCO$_2$ and pH awake values at room air. In patients 4 and 9 respiratory tests were not performed due to pneumothoraces.
L—L = left lung,
R-L = right lung,
L = lower lobe,
U = upper lobe,
M = median lobe.
Mini-CABG = minimal invasive coronary by-pass graft.

ARS Protocol:
1. Inspiratory time was increased to 50%.
2. Respiratory frequency was set to 12 breaths/min.
3. The inspiratory pressure gradient was limited to 20 cmH$_2$O in order to avoid large tidal volumes during the maneuver. PIP and PEEP were sequentially increased from 30/10 to 35/15 in steps of five breaths. The recruitment pressure of 40/20 cmH$_2$O was applied for 10 breaths.
4. Airway pressures were then gradually decreased, returning to baseline settings but maintaining a PEEP level of 8 cmH$_2$O.

After completing the ARS, the ventilator was set back to volume control. The ARS took about 3 minutes. Prior to the recruitment maneuvers central venous pressure values were maintained above 10 mmHg to avoid hemodynamic side effects caused by the increased intrathoracic pressures. Hemodynamic and ventilatory variables were monitored closely while performing the ARS. If mean arterial pressure and/or heart rate changed by more than 15% from baseline, the ARS was discontinued and 500 ml of crystalloid solution were administered. After regaining hemodynamic stability the ARS was tried again.

During surgery, oxygen saturation was maintained above 90% at all times. If during OLV SpO$_2$ fell below 90%, surgery was temporarily interrupted to resume TLV (intermittent ventilation) until oxygen saturation recovered to at least 97%. Blood samples were processed within 5 minutes of extraction by the blood gas analyzer known as ABL 520 and values were corrected for body temperature. The calibration this device was done with the same CO$_2$ concentration as capnograph (5%).

The following table shows the results with regard to the most relevant tracing values and at three different lung stages:

| Variables | TLV | OLV before ARS | OLV after ARS |
|---|---|---|---|
| Absolute values (ml): | | | |
| VD$^{aw}$ | 160 ± 28 | 123 ± 29* | 107 ± 30† |
| VD$^{alv}$ | 106 ± 31 | 107 ± 24 | 97 ± 23 |
| VD$^{phys}$ | 266 ± 42 | 230 ± 39 | 204 ± 34† |
| VT$^{alv}$ | 392 ± 42 | 260 ± 39* | 279 ± 40† |
| VTCO$_{2,br}$ | 19 ± 2.8 | 13 ± 2.7 | 14 ± 2.5 |
| Ratios: | | | |
| VD/VT | 0.50 ± 0.04 | 0.60 ± 0.05* | 0.53 ± 0.04† |
| VD$^{aw}$/VT | 0.30 ± 0.05 | 0.33 ± 0.07 | 0.29 ± 0.08 |
| VD$^{alv}$/VT$^{alv}$ | 0.28 ± 0.07 | 0.43 ± 0.1* | 0.35 ± 0.07 |
| Vol I/VT | 0.23 ± 0.03 | 0.24 ± 0.06 | 0.19 ± 0.04‡ |
| Vol II/VT | 0.29 ± 0.05 | 0.30 ± 0.05 | 0.25 ± 0.04‡ |
| Vol III/VT | 0.48 ± 0.07 | 0.47 ± 0.1 | 0.56 ± 0.07‡ |
| Slope II (%/L) | 16 ± 3.5 | 15 ± 3.9 | 18 ± 3.9 |
| Slope III/N (1/L) | 0.58 ± 0.3 | 1.08 ± 0.3* | 0.72 ± 0.2‡ | wherein:
TLV = two lung ventilation
OLV$_{PRE}$ = one lung ventilation before the recruitment maneuver
OLV$_{ARS}$ = one lung ventilation after an alveolar recruitment strategy (ARS).
VD$^{aw}$ = airway dead space
VD$^{alv}$ = alveolar dead space
VD$^{phys}$ = physiological dead space.
VT$^{alv}$ = alveolar tidal volume
VTCO$_{2,br}$ = expired volume of CO$_2$ per breath
VD/VT = physiological dead space to tidal volume

| Variables | TLV | OLV before ARS | OLV after ARS |
|---|---|---|---|

$VD^{aw}/VT$ = airway dead space to tidal volume
$VD^{alv}/VT^{alv}$ = alveolar dead space to alveolar tidal volume, Vol I, II and III/VT = volume of phase I, II and III to tidal volume respectively, slope II = phaee II slope (%/L) and slope III/N = normalized phase III slope (1/L) dividing absolute value by the mean alveolar fraction of $CO_2$ ($FAECO_2$, in %).
The physiological dead space ($VD^{phy}$) was calculated by Enghoff's modification of the Bohr equation, where $VD^{phy}/VT = PaCO_2 - PAECO_2/PaCO_2$. Alveolar dead space ($VD^{alv}$) was calculated by subtracting physiological from airway dead space.
*TLV against $OLV_{PRE}$, p < 0.05;
†$OLV_{ARS}$ against TLV, p < 0.05; and
‡$OLV_{ARS}$ against $OLV_{PRE}$, p < 0.05.

Figure 10:
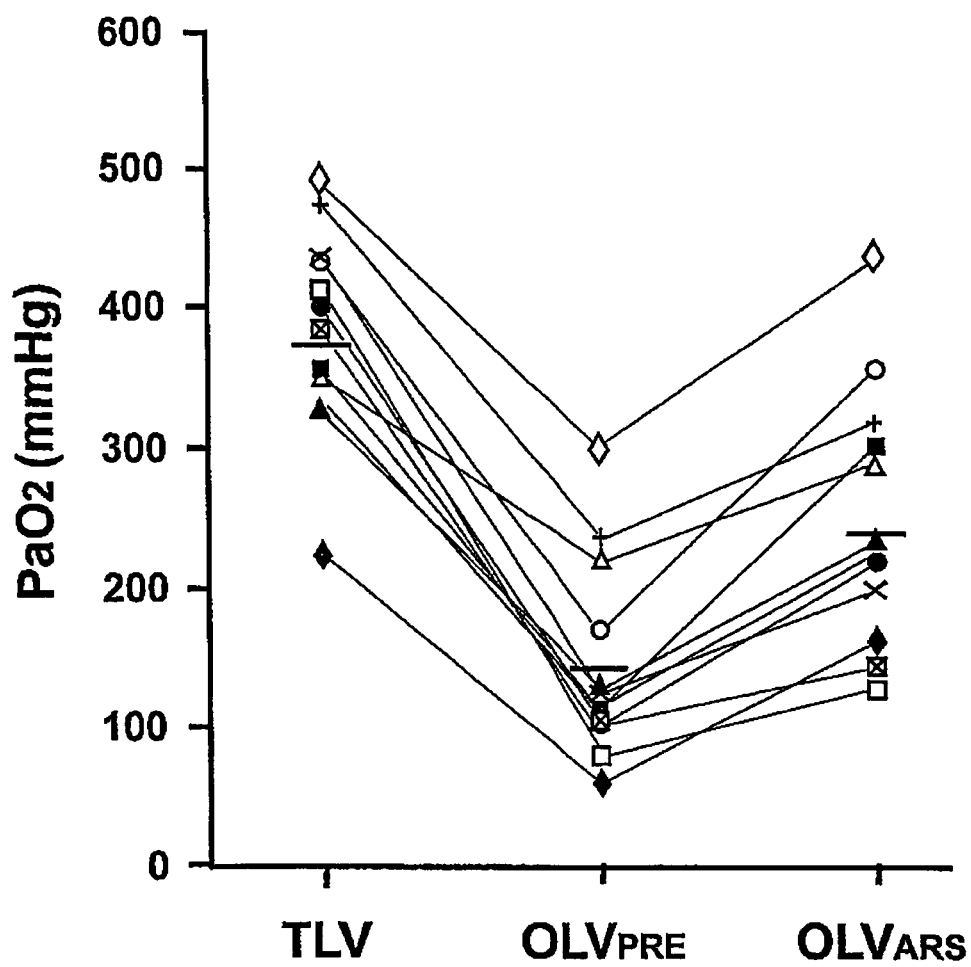
FIG. 10 shows measurements of the partial pressure of oxygen ($paO_2$) with 12 patients at three different lung stages.

FIG. 10 shows measurements of the partial $paO_2$ pressure with 12 patients at three different lung stages.

$PaO_2$ was significantly higher during TLV (379±67 mmHg) compared to $OLV_{PRE}$ (144±73 mmHg, p<0.001) and $OLV_{ARS}$ (244±89 mmHg, p<0.001). During OLV the difference in $PaO_2$ before and after the ARS also reached significance. Hemoglobin $O_2$ saturation was lower at $OLV_{PRE}$ (95.5±2.6%) as compared to TLV (98.7±0.4%, p<0.001) and $OLV_{ARS}$ (97.8%±0.9%, p<0.01).

Only patients 8 needed 4 cycles of intermittent ventilation during OLV before the ARS ($SpO_2$<90%). Blood gases were taken after the fourth cycle of intermittent TLV immediately before the recruitment maneuver. In these patients the ARS relieved the arterial hypoxemia instantaneously, ($SpO_2$ from 88% to 98%) and no more episodes of hemoglobin desaturation occurred.

$PaCO_2$ was 43±6 mmHg during $OLV_{ARS}$ but not significantly different from the other conditions. However, $PaCO_2$ was higher during $OLV_{PRE}$ (46±6 mmHg) compared to TLV (38±4 mmHg, p<0.05). $EtCO_2$ and $PAECO_2$ were stable during the protocol without any significant differences among the measurement points. Pa-$etCO_2$ difference was significant higher during $OLV_{PRE}$ (14.2±4.8 mmHg) compared to TLV (8.8±3.2 mmHg) and $OLV_{ARS}$(11.6±4.6 mmHg). The pHa remained in the normal range throughout the study period.

All mean tracing values (variables) listed in the table above decreased during $OLV_{ARS}$ compared to $OLV_{PRE}$, but differences showed statistical significance only for VD/VT, Vol I, II, III/VT and phase III slope.

Tidal volumes were higher during TLV (506±83 ml) compared to $OLV_{PRE}$ (377±45 ml) and $OLV_{ARS}$ (382±42 ml). Minute ventilation was similar between $OLV_{PRE}$ (5.9 l/min) and $OLV_{ARS}$ (5.8 l/min), but both values were significantly smaller than during TLV (7 l/min). PIP values were higher during $OLV_{PRE}$ (25.3±1.7 cm$H_2O$) compared with TLV (20.6±1.7 cm$H_2O$, p<0.001) and $OLV_{ARS}$ (23.2±2 cm$H_2O$, p<0.05) with no differences between the latter two.

Hemodynamic variables, minute $CO_2$ elimination, oxygen consumption and respiratory quotient were similar at all time points. The total time of OLV ranged from 50 to 105 minutes. No hemodynamic or ventilatory side effects related to the recruitment maneuver were detected.

The results of this study indicate an improved efficiency in gas exchange after a lung recruitment maneuver during OLV. This finding can be explained by a recruitment effect on both, shunt and dead space, taking into account that hemodynamic, metabolic and ventilatory conditions were stable along the protocol.

Arterial oxygenation is a common measurement used to describe the extent of lung collapse. It has been suggested that a $PaO_2$ higher than 450 mmHg defines an open lung condition during pure $O_2$ breathing. Arterial oxygenation, however, is an unspecific variable to evaluate the recruitment effect since it depends on the hemodynamic and metabolic status. As these two conditions remained stable throughout the study period, a true recruitment effect is the most likely explanation for the increases seen in $PaO_2$.

During TLV a mean $PaO_2$ of 379±67 mmHg indicated some extent of lung collapse, which is a common finding during general anesthesia. Oxygenation was further impaired during $OLV_{PRE}$ but increased after recruiting the dependent lung.

At TLV, the calculated shunt values of the patients ranged from 8 to 22% (mean 16%), values typically seen in general anesthesia, during OLV from 18 to 45% (mean 28%) and during $OLV_{ARS}$ from 12 to 27% (mean 21%). After lung recruitment oxygenation was sufficient to maintain hemoglobin saturation above 95%.

$PaCO_2$ increased during OLV at the same $etCO_2$ and $PAECO_2$ values as those observed during TLV. Increases in deadspace during OLV can explain this decrease in the efficiency of $CO_2$ removal.

During TLV, the values of the dead space related tracing values are higher than normal, due to the double lumen tube, lung collapse, open-chest condition, and the use of positive pressure ventilation.

Surprisingly, alveolar dead space did not change during OLV despite a significant increase in shunt. There is no explanation for the absence of an increase in $VD^{alv}$ despite a marked shunt effect (apparent dead space) during OLV compared to TLV. It is assumed that during TLV a decrease in the perfusion of the nondependent lung can increase $VD^{alv}$ (real alveolar dead space) despite a lower shunt.

Large tidal values during TLV result also in absolute large values for $VD^{aw}$, $VT^{alv}$ and $VD^{phys}$ larger than the ones observed during OLV, thus making their direct comparison questionable. Nevertheless, when these tracing values (variables) are adjusted to account for differences in tidal volume this comparison may become useful.

The tracing values (variables) that represent efficiency of ventilation and $CO_2$ exchange ($VCO_{2,br}$, VD/VT, Pa-$etCO_2$, $VT^{alv}$, $vD^{alv}/VT^{alv}$) were higher during TLV compared to OLV. During OLV all tracing values (variables) improved only after the recruitment maneuver. Even more interesting was the behaviour of the tracing values (variables) that show the distribution of tidal volume throughout the phases of the $CO_2$ single breath test. Distribution of volume was most efficient during OLV after the ARS as indicated by a decrease in phase I and II volumes and a concomitant increase in phase III volume. The absolute value of the ratio Phase III/VT observed after recruitment was even higher than during TLV. Phase II represents a transition between alveolar and airway gas transport. An increase in the cross-sectional area of the bronchial tree in the lung periphery decreases the linear velocity of the bulk flow until a point where the two transport mechanisms within the lungs (convection and diffusion) are of equal magnitude. This stationary diffusion front demarcates the transition between airway and alveolar gas. On expiration, this front corresponds to phase II and is used to measure $VD^{aw}$ in Fowler's analysis.

Changes in inspiratory flow, tidal volume and peripheral cross-sectional area of bronchioli have an effect on the diffusion front, and thus on the volume and slope of phase II. If inspiratory flow and tidal volume are constant, as during OLV, any change in phase II must be interpreted as a recruitment related increase in the cross-sectional area of the bronchioli leading to a more homogeneous gas emptying of lung acini. The slope of phase II, which depends on the spread of transit time of different lung units, increased during OLV after the recruitment maneuver when compared to the other study conditions. However, differences were not significant. This increase in phase II slope in combination with a decrease in its volume, can be considered as a more synchronous and homogeneous emptying of acini during expiration. Both, asthma and emphysema would have an opposite effect on phase II. These conditions show a wide dispersion of the transit time of gas emptying among lung units making the slope of phase II flatter and its volume higher.

Diffusion is the most important mechanism of gas transport within the acinus. Phase III volume represents the amount of gas exposed to the capillary bed and therefore depends on an effective pulmonary perfusion and $CO_2$ production. Phase III slope is directly related to the V/Q relationship and represents the diffusional resistance for $CO_2$ at the alveolar-capillary membrane. Its positive slope is explained by lung pendelluft, continuous evolution of $CO_2$ from the blood into the acini, and a stratified inhomogeinity.

As could have been expected, during $OLV_{ARS}$, phase III volume increased while its slope decreased compared to $OLV_{PRE}$. Decrease in functional lung acini in emphysema is related to an increase in phase III slope.

The patients included in the study were submitted to different thoracic surgeries including classical thoracotomies (lobectomies), minimal invasive thoracotomies (mini-CABG), and closed-chest surgeries (Thoracoscopies). Possible differences in lung mechanics can account for the changes in arterial oxygenation and ventilation efficiency among these different type of surgeries. However, oxygenation and dead space behaviour were similar and hemodynamic and metabolic conditions were constant along the study period. For these reasons, it is assumed that the changes in gas exchange and dead space observed in the study were related to the therapeutic effect of the recruitment maneuver.

Epidural anesthesia used in open thoracotomies can cause hemodynamic and metabolic changes that could influence gas exchange. However, these conditions were stable and no differences in $PaO_2$ between open thoracotomies and thoracoscopies, without epidural anesthesia, were seen.

Empirical values of 40 $cmH_2O$ of PIP were used as opening pressure and 8 $cmH_2$ of PEEP to keep the lung open, since individual levels of these pressures for each patient are difficult to determine at the bedside.

Due to a mediastinal displacement, the surgeon's manipulation and the chest fixation opening and closing pressures in the dependent lung could be higher during thoracic surgery as compared to the other types of surgeries. In addition, PIP pressure may not represent true alveolar pressure when using a narrow DLT. For these reasons, it is possible that true opening and closing pressures were not reached in each patient which could have resulted in the absence of the maximal impact of the ARS on oxygenation and lung efficiency.

Lung recruitment improves gas exchange and ventilation efficiency during OLV anesthesia. The results suggest that one simple recruitment maneuver during OLV is enough to increase $PaO_2$ to safer levels thereby eliminating the need for any additional therapeutic intervention.

In the following, a second study concerning the effect of PEEP on dead space, with and without a lung recruitment maneuver, is discussed.

Sixteen patients were studied prospectively undergoing open lower abdominal surgery. The enrolled patients were patients ASA II-III, without smoking history or cardiopulmonary uncompensated diseases.

Anesthesia induction was performed with fentanyl 4 µg $kg^{-1}$, thiopental 3 mg $kg^{-1}$ and vecuronium 0.08 mg $kg^{-1}$ and maintained with Isofluorane and bupivacaine 0.5% through an epidural catheter inserted at L2-3.

After tracheal intubation with a cuffed endotracheal tube, the lungs were ventilated with a Siemens 900 C ventilator (Siemens-Elema, Solna, Sweden). Air leaks from around the endotracheal tube were detected by comparing inspired-expired tidal volume (VT) measured proximally in the airway. A volume controlled mode was used with a VT of 8 ml $kg^{-1}$, respiratory rate (RR) between 10-15 bpm, $FIO_2$ of 0.5, inspiratory time of 0.3 without pause and initially, without positive end-expiratory pressure (ZEEP). Alveolar ventilation was increased or decreased by adjusting RR to reach an end-tidal $CO_2$ value of 34 mmHg while maintaining VT constant.

Static respiratory compliance was measured dividing VT by the pressure differences between plateau and total PEEP. End-expiratory lung volume (EELV) was measured pushing the expiratory pause button of the Servo 900C for 6 seconds during the inspiratory pause while releasing PEEP from 5 $cmH_2O$ to ZEEP. Thus, a volume of gas is expelled until FRC at ambient pressure is reached. The EELV was then determined by subtracting the average value of the latest three normal expiratory tidal volumes before the maneuver from the volume of gas measured. This volume was recorded continuously in a computer and analyzed it off-line. The return of the expiratory flow curve to baseline at the end of the EELV-maneuver was used for checking air trapping.

Figure 6:
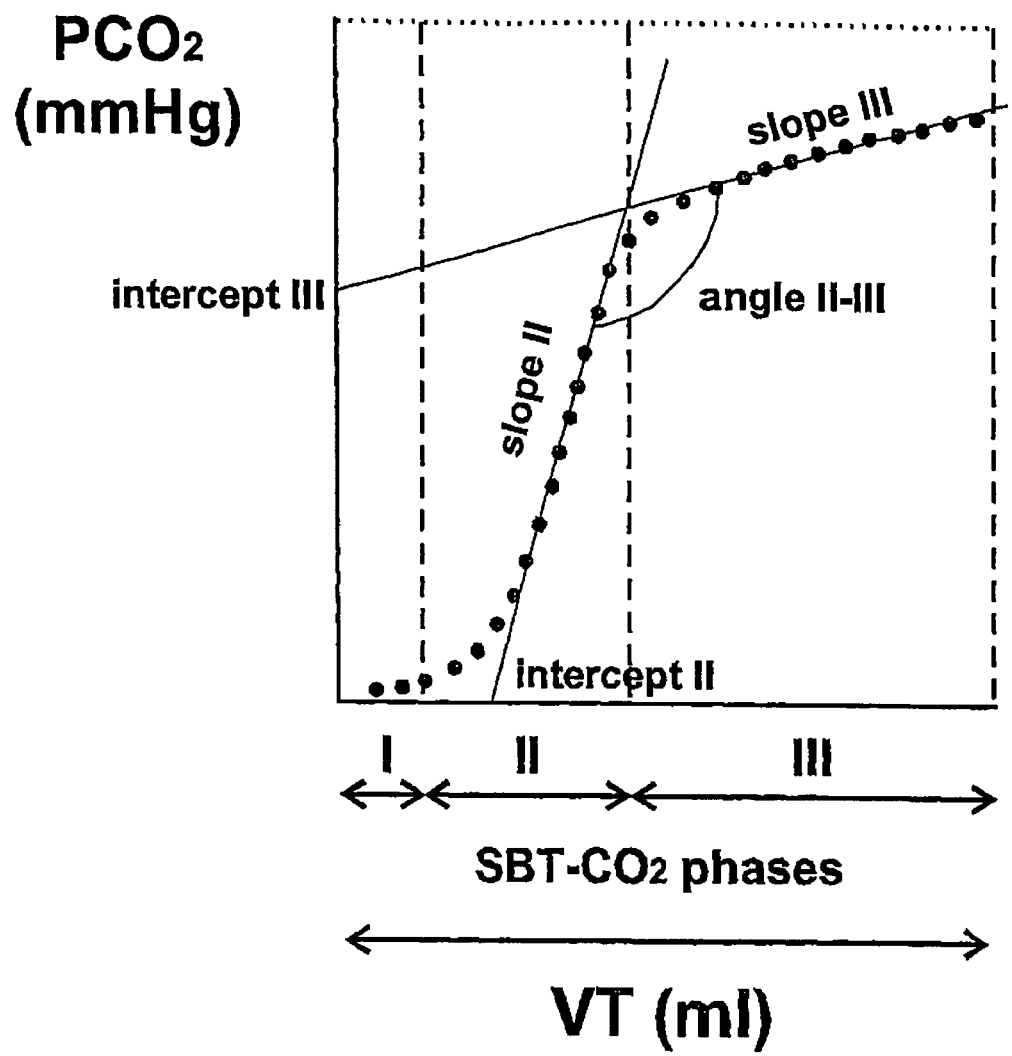
FIG. 6 shows some possible tracing values within a plot of a $CO_2$ single breath test.

Carbon dioxide elimination ($VCO_2$) was calculated by multiplying alveolar ventilation and mean alveolar fraction of $CO_2$. Oxygen consumption ($VCO_2$) was calculated as the product of alveolar ventilation and inspiratory-expiratory $O_2$ difference. The respiratory quotient (RQ) was calculated dividing $VCO_2$ by $VO_2$. The $CO_2$ single breath test and its tracing values are explained according to FIG. 3 and FIG. 6 above.

The ventilatory, hemodynamic and metabolic states were maintained constant during the study. In each patient 3 periods were studied sequentially:
1. ZEEP: ventilation with zero of PEEP.
2. PEEP: ventilation with 5 $cmH_2O$ of PEEP.
3. ARS: Between point 2 and 3, the lungs were ventilated for 20 minutes without PEEP to reach baseline conditions once again.

Figure 1:
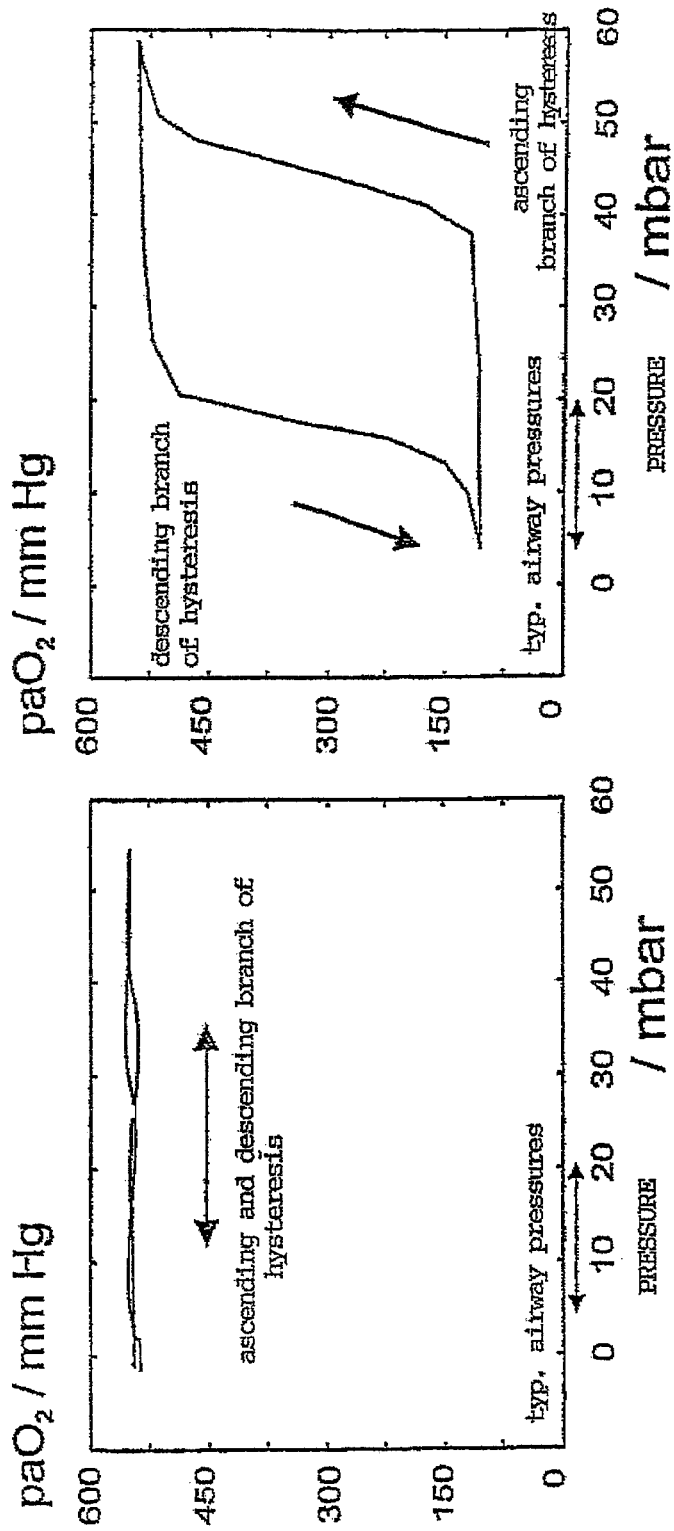
FIG. 1 shows two graphs of the $paO_2$ hysteresis of the same healthy (left) and ailing (right) lung.
Figure 2:
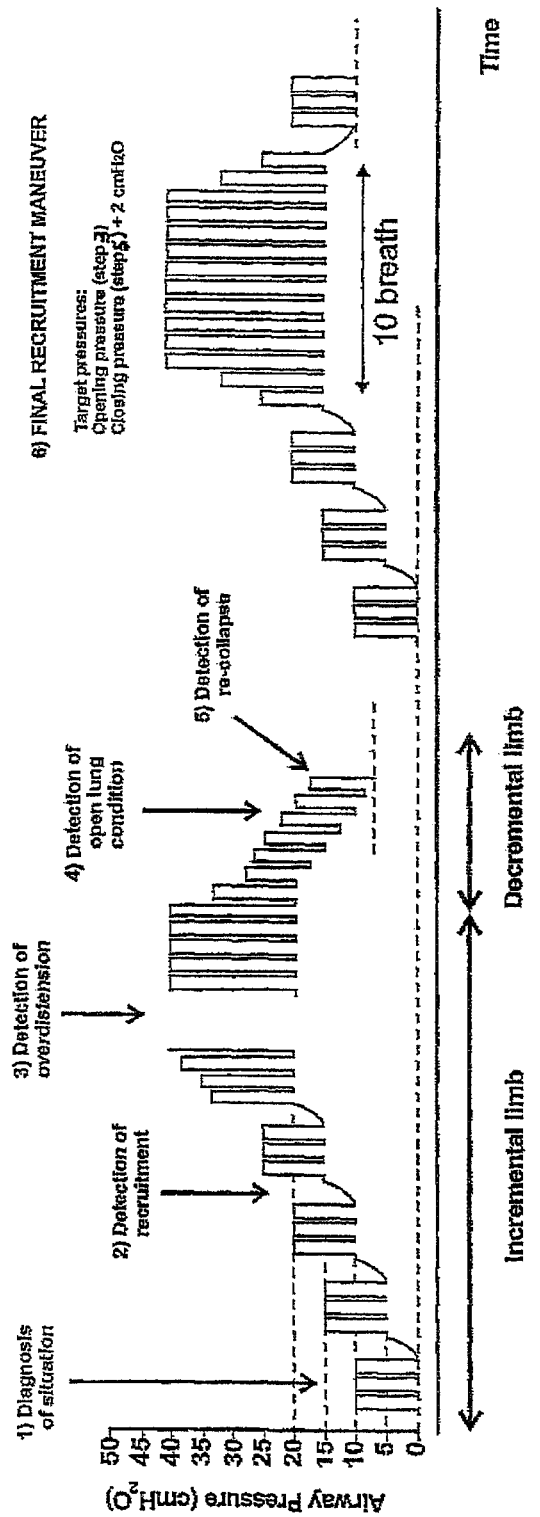
FIG. 2 shows a plot of the airway pressures over time of a typical recruitment maneuver.

The alveolar recruitment strategy is a maneuver assigned to treat pulmonary collapse by reaching the alveolar opening pressure for ten breaths and keeping the lung open with a PEEP level above the lung's closing pressure. In the patients studied it is assumed that the lung opening pressure was 40 $cmH_2O$ of peak inspiratory pressure (PIP) and the closing pressure lower than 5 $cmH_2O$. The maneuver was performed according to FIG. 2 with the following settings:

Ventilatory frequency was set to 15 breaths per minute.
Inspiration/expiration ratio was set at 1:1.
Delta pressure or the pressure difference between PIP and PEEP (PIP/PEEP) was maintained at 20 $cmH_2O$.
Airway pressures were increased in steps: 25/5 to 30/10 and then to 35/15 $cmH_2O$. Each step of pressure was maintained for 5 breaths.
A final PIP/PEEP step of 40/20 $cMH_2O$ was reached and maintained for 10 breaths.
After the 10 breaths, airway pressures were gradually decreased returning to the previous setting at 5 $cmH_2O$ of PEEP reassuming a volume controlled ventilation mode.

At the end of each period (30 minutes), the $CO_2$ single breath test curves were recorded and blood samples taken for dead space analysis. Blood specimens were processed and corrected for body temperature within 5 minutes of extraction by a gas analyzer ABL 510. Body temperature was measured with an esophageal thermometer.

Comparison of tracing values (variables) among periods was carried out using analysis of variance. If the variance F-statistic was significant the Student-Newman-Keuls post-test detected significant differences. EELV between PEEP and ARS was evaluated by the Student t test. Values are reported as mean±SD and a p<0.05 was considered significant.

Nine females and seven males, aged 65-80 years (71.2±4.5), with body mass indices between 24-30 (26.8±2.1) undergoing hysterectomies (n=3) and hemicolectomies (n=13) were studied. The following table shows the detected tracing values (variables) with regard to the three different ventilation modes ZEEP, PEEP and ARS, where:

| Variable | ZEEP | PEEP | ARS |
|---|---|---|---|
| $V_D/V_T$ | 0.50 ± 0.07 | 0.51 ± 0.06 | 0.45 ± 0.01*† |
| $V_{D\,AW}$ (ml) | 160 ± 48 | 161 ± 38 | 137 ± 32 |
| $V_{D\,ALV}$ (ml) | 110 ± 35 | 113 ± 30 | 108 ± 32 |
| $V_{D\,PHYS}$ (ml) | 270 ± 54 | 274 ± 56 | 246 ± 50 |
| $V_{D\,ALV}/V_{TALV}$ | 0.29 ± 0.05 | 0.28 ± 0.06 | 0.26 ± 0.04 |
| $V_{D\,AW}/V_T$ | 0.30 ± 0.08 | 0.29 ± 0.04 | 0.25 ± 0.04‡† |
| $V_T CO_{2,br}$ (ml) | 23 ± 2.6 | 25 ± 3.3* | 27 ± 3.2‡† |
| $V_{T\,ALV}$ (ml) | 340 ± 72 | 355 ± 71 | 373 ± 68‡† |
| Vol I/$V_T$ | 0.22 ± 0.09 | 0.21 ± 0.06 | 0.18 ± 0.06 |
| Vol II/$V_T$ | 0.35 ± 0.05 | 0.28 ± 0.05* | 0.26 ± 0.05† |
| Vol III/$V_T$ | 0.45 ± 0.08 | 0.51 ± 0.1* | 0.57 ± 0.09‡† |
| Slope II (%/L) | 46 ± 7.7 | 56 ± 10* | 63 ± 11‡† |
| Slope III/N (L$^{-1}$) | 0.21 ± 0.11 | 0.18 ± 0.10* | 0.13 ± 0.07‡† |
| Angle II/III (°) | 127 ± 2.1 | 125 ± 7.7 | 113 ± 4‡† |

VD/VT = physiologic dead space to tidal volume
VDAW = airway dead space (ml)
VDALV = alveolar dead space (ml)
VDPHYS = physiologic dead space (ml)
VDAW/VTALV = alveolar dead space to tidal volume
VDAW/VT = airway dead space to tidal volume
VTCO$_{2,br}$ = CO$_2$ elimination per breath (ml)
VTALV = alveolar tidal volume (ml)
Vol I/VT = volume of phase I to tidal volume
Vol II/VT = volume of phase II to tidal volume
Vol III/VT = volume of phase III to tidal volume
slope II = phase II slope
slope III/N = normalized phase II slope divided by the mean alveolar concentration of CO$_2$
angle II/III = angle formed between phase II and III slopes (°).
*PEEP against ZEEP, p < 0.05
†ARS against ZEEP, p < 0.05
‡ARS against PEEP, p < 0.05.
Values are presented as mean ± SD. A p value lower than 0.05 was considered significant.

Lung recruitment increased tracing values related to lung efficiency and decreased tracing values related to inefficiency. PEEP did not have same effect on dead space. Phase II slopes showed a significant increase with PEEP and ARS although lung recruitment showed the highest values. These steeper slopes were associated with a corresponding decrease in Vol II/VT.

Normalized phase III slope decreased with PEEP ventilation and showed an additional diminution after ARS. Volume of phase III increased with ARS and PEEP compared with ZEEP. The angle between II-III showed significant differences only after the recruitment maneuver.

The following table shows partial pressures of CO$_2$ and the alveolar ventilation at constant minute ventilation.

| Variable | ZEEP | PEEP | ARS |
|---|---|---|---|
| PaCO$_2$ (kPa) | 5.1 ± 0.4 | 5.2 ± 0.6 | 4.9 ± 0.5 |
| etCO$_2$ (kPa) | 4.0 ± 0.3 | 4.0 ± 0.4 | 3.9 ± 0.2 |
| Pa-etCO$_2$ (kPa) | 1.1 ± 0.5 | 1.2 ± 0.5 | 0.9 ± 0.5*† |
| $\dot{V}$A (l/min) | 3.3 ± 0.8 | 3.4 ± 0.6 | 3.6 ± 0.8*† |

PaCO$_2$ = arterial partial pressure of CO$_2$ (kPa)
etCO$_2$ = end-tidal partial pressure of CO$_2$ (kpa)
Pa-etCO$_2$ = arterial to end-tidal differences of CO$_2$ (kPa)
VA = alveolar minute ventilation (l/min).
*ARS against ZEEP, p < 0.05
†ARS against PEEP, p < 0.05.
Pa-etCO$_2$ was significantly lower and alveolar ventilation larger after ARS compared with ZEEP and PEEP.

Figure 11:
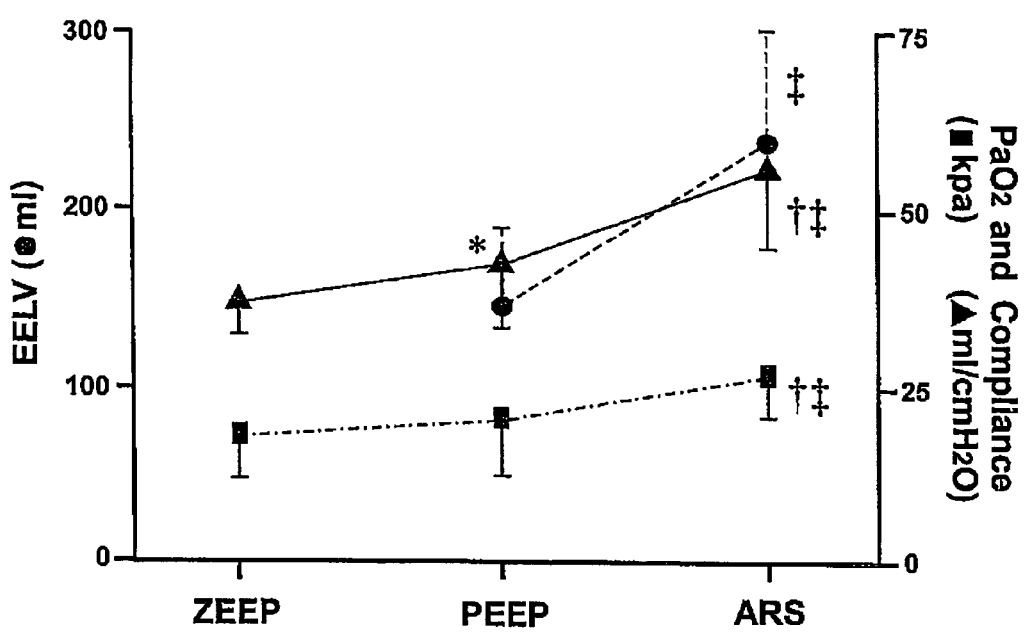
FIG. 11 shows measurements of the end-expiratory lung volume (EELV), the partial pressure of oxygen ($paO_2$) and the compliance at three different ventilation modes.

FIG. 11 shows measurements of the end-expiratory lung volume (EELV), the partial paO$_2$ pressure and the compliance at three different ventilation modes. Arterial oxygenation, EELV and respiratory compliance showed a significant increase after lung recruitment compared with ZEEP and PEEP. PEEP without lung recruitment showed compliance values significantly higher than ZEEP but without changes in PaO$_2$.

When compared with ZEEP or PEEP, lung recruitment decreased those tracing values of the CO$_2$ single breath test which are related to pulmonary inefficiency and increased the ones related to efficiency. The increased efficiency of ventilation was associated with an increase in arterial oxygenation, expiratory lung volume and respiratory compliance, all parameters commonly used as markers of an open lung condition.

PEEP without recruitment showed an intermediate effect between ZEEP and ARS in all tracing values studied. In anaesthetized patients low levels of PEEP have a contradictory effect on arterial oxygenation and atelectasis. Study results agree in that the recruitment of collapsed airways is the main effect of PEEP without a recruitment maneuver. Atelectasis treatment requires higher airway pressures than the amount of PEEP commonly used during anesthesia to pop open collapsed alveoli due to the incomplete lung recruitment observed with the use of PEEP alone.

In contrast to PEEP alone, lung recruitment maneuver increase both, the cross-sectional area of small airways and the alveolar-capillary area, by reversing airway and acinar collapse respectively. This total recruitment or open lung condition improves the diffusive CO$_2$ transport at the acinar level and could explain the changes observed in the CO$_2$ single breath test. Increasing CO$_2$ diffusion after the ARS moves the interface between convective-diffusive transport mouthward, thus decreasing the VDAW measured by Fowler's method.

Lung recruitment was also associated with an improved efficiency in CO$_2$ elimination as expressed by a larger VTCO$_{2,br}$ and a lower Pa-etCO$_2$ at constant VCO$_2$ and ventilator settings. These results indicate that the area of gas exchange increased and V/Q improved.

Differences between PEEP and ARS in the distribution of gas volumes within the lung may have an impact on gas exchange and respiratory compliance. Analyzing EELV and the volumes of phase I-II-III, it was observed that the recruitment maneuver re-distributed the VT away from phase I-II towards the volume of phase III (alveolar gas). Compared with ZEEP, PEEP without a recruitment maneuver increased volume of phase III but at the same time, retained some volume within the inefficient parts of the VT (phase I and II).

Changes in the slope of phase II and III at ZEEP could be explained by the co-existence of acini with different time constants due to aging and partial collapse.

Total lung recruitment has a positive effect on $CO_2$ diffusion as reflected by the changes observed in volumes and slopes of phase II-III after ARS. On the one hand it is assumed that an increase in the cross-sectional area caused by airway recruitment could improve the $CO_2$ diffusive transport from alveoli to bronchioli. On the other hand, an increase in the area of gas exchange due to a recruitment of atelectasis improved the diffusive transport from the capillaries to the alveoli.

In summary, the alveolar recruitment strategy improved the efficiency of ventilation in anesthetized patients. Differences observed in the $CO_2$ single breath test between PEEP with and without an lung recruitment maneuver can be explained by the effectiveness of the treatment of pulmonary collapse.

Figure 12:
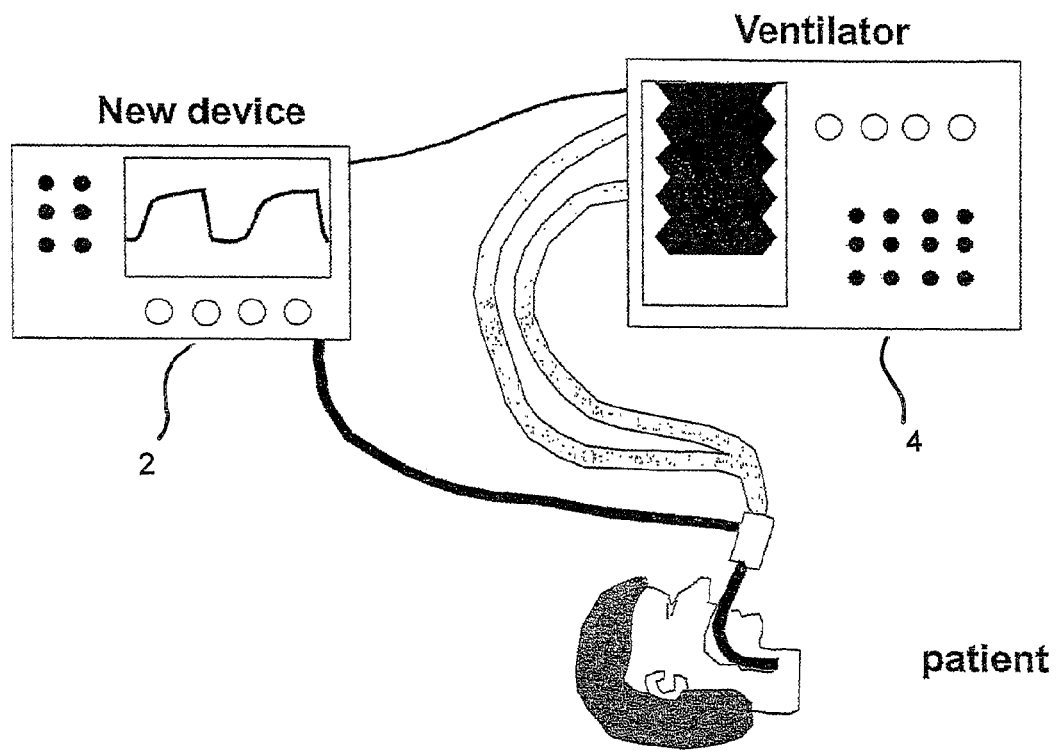
FIG. 12 shows a draft of an apparatus according to the invention connected in series with the ventilator to the patient.

FIG. 12 shows an apparatus 2 according to the invention connected in series with the ventilator 4 to the patient. The apparatus comprises a carbon dioxide sensor for measuring is the expired $CO_2$ concentration, a pneumotachograph for measuring airway flow, a pressure sensor for measuring airway pressures, and a data processor which determines during a change of the airway pressure from the resulting course of at least one tracing value the airway pressure level at which alveolar opening or lung overdistension or lung open condition or alveolar closing occurs. As indicated in FIG. 12, a feedback line can be included connecting the apparatus with the ventilator thus creating effectively a closed loop system. This allows to directly control the ventilator, once the optimal values for PIP and PEEP have been identified.

As an example, with regard to the above-mentioned tracing values the following logic can be implemented in the data processor:

Detection of Lung Recruitment

The peak inspiratory pressure is increased continuously and a lung opening is detected, if the slope of phase III reaches a maximal decrease.

The peak inspiratory pressure is increased continuously and a lung opening is detected, if the intercept of the slope of phase III reaches a maximal increase.

The peak inspiratory pressure is increased continuously and a lung opening is detected, if the slope of phase II reaches a maximal increase.

The peak inspiratory pressure is increased continuously and a lung opening is detected, if the intercept of slope of phase II reaches a maximal decrease.

The peak inspiratory pressure is increased continuously and a lung opening is detected, if the angle II-III reaches a maximal decrease.

The peak inspiratory pressure is increased continuously and a lung opening is detected, if the volume of phase I reaches a maximal increase.

The peak inspiratory pressure is increased continuously and a lung opening is detected, if the volume of phase II reaches a maximal increase.

The peak inspiratory pressure is increased continuously and a lung opening is detected, if the volume of phase III reaches a maximal decrease.

The peak inspiratory pressure is increased continuously and a lung opening is detected, if the $VTCO_{2,br}$ reaches a maximal increase.

The peak inspiratory pressure is increased continuously and a lung opening is detected, if the $VCO_2$ reaches a maximal increase.

The peak inspiratory pressure is increased continuously and a lung opening is detected, if the VDbohr reaches a maximal decrease.

The peak inspiratory pressure is increased continuously and a lung opening is detected, if the negative gradient of the resulting course of the measured $etCO_2$ minus the mean alveolar partial pressure of $CO_2$ (Pet-$AECO_2$) reaches the maximal decrease.

Detection of Lung Overdistension

The peak inspiratory pressure is increased continuously and a lung overdistension is detected, if the VDaw reaches a maximal increase, provided the maximal peak inspiratory pressure is below a preset maximal peak inspiratory pressure defined by the user and above a preset minimal peak inspiratory pressure defined by the user.

The peak inspiratory pressure is increased continuously and a lung overdistension is detected, if the Vdaw/VT reaches a maximal increase, provided the maximal peak inspiratory pressure is below a preset maximal peak inspiratory pressure defined by the user and above a preset minimal peak inspiratory pressure defined by the user.

The peak inspiratory pressure is increased continuously and a lung overdistension is detected, if the $VTCO_{2,br}$ results in a decrease of about 10% from its previous value, provided the maximal peak inspiratory pressure is below a preset maximal peak inspiratory pressure defined by the user and above a preset minimal peak inspiratory pressure defined by the user.

The peak inspiratory pressure is increased continuously and a lung overdistension is detected, if the VCO2 results in a decrease of about 10% from its previous value, provided the maximal peak inspiratory pressure is below a preset maximal peak inspiratory pressure defined by the user and above a preset minimal peak inspiratory pressure defined by the user.

The peak inspiratory pressure is increased continuously and a lung overdistension is detected, if the PAECO2 results in a decrease of about 10% from its previous value, provided the maximal peak inspiratory pressure is below a preset maximal peak inspiratory pressure defined by the user and above a preset minimal peak inspiratory pressure defined by the user.

The peak inspiratory pressure is increased continuously and a lung overdistension is detected, if the angle II-II results in a decrease of about 10% from its previous value, provided the maximal peak inspiratory pressure is below a preset maximal peak inspiratory pressure defined by the user and above a preset minimal peak inspiratory pressure defined by the user.

The peak inspiratory pressure is increased continuously and a lung overdistension is detected, if the phase II slope results in a decrease of about 10% from its previous value, provided the maximal peak inspiratory pressure is below a preset maximal peak inspiratory pressure defined by the user and above a preset minimal peak inspiratory pressure defined by the user.

Detection of Open-Lung Condition

The positive end expiratory pressure is decreased continuously and an open-lung condition is detected, if the VDaw resulting in a minimal value observed before the closing pressure is detected.

The positive end expiratory pressure is decreased continuously and an open-lung condition is detected, if the vDaw/VT resulting in a minimal value observed before the closing pressure is detected.

The positive end expiratory pressure is decreased continuously and an open-lung condition is detected, if the $VTCO_{2,br}$ resulting in a maximal value observed before the closing pressure is detected.

The positive end expiratory pressure is decreased continuously and an open-lung condition is detected, if the angle II-III resulting in a minimal value observed before the closing pressure is detected.

The positive end expiratory pressure is decreased continuously and an open-lung condition is detected, if the phase II slope resulting in a maximal value observed before the closing pressure is detected.

The positive end expiratory pressure is decreased continuously and an open-lung condition is detected, if the Volume of phase II resulting in a minimal value observed before the closing pressure is detected.

The positive end expiratory pressure is decreased continuously and an open-lung condition is detected, if the Volume of phase III resulting in a maximal value observed before the closing pressure is detected.

The positive end expiratory pressure is decreased continuously and an open-lung condition is detected, if the intercept of phase II slope resulting in a maximal value observed before the closing pressure is detected.

Detection of Lung Re-Collapse

The positive end expiratory pressure is decreased continuously and a closing pressure of the lungs is detected, if the curve of the tracing values of the VDaw shows a permanent gradient change after the point corresponding to the open-lung condition values, provided the closing pressure is below a preset maximum positive end expiratory pressure defined by the user and above a preset minimum positive end expiratory pressure defined by the user.

The positive end expiratory pressure is decreased continuously and a closing pressure of the lungs is detected, if the curve of the tracing values of the $VTCO_{2,br}$ shows a permanent gradient change after the point corresponding to the open-lung condition values, provided the closing pressure is below a preset maximum positive end expiratory pressure defined by the user and above a preset minimum positive end expiratory pressure defined by the user.

The positive end expiratory pressure is decreased continuously and a closing pressure of the lungs is detected, if the curve of the tracing values of the $VCO_2$ shows a permanent gradient change after the point corresponding to the open-lung condition values, provided the closing pressure is below a preset maximum positive end expiratory pressure defined by the user and above a preset minimum positive end expiratory pressure defined by the user.

The positive end expiratory pressure is decreased continuously and a closing pressure of the lungs is detected, if the curve of the tracing values of the volume of phase II shows a permanent gradient change after the point corresponding to the open-lung condition values, provided the closing pressure is below a preset maximum positive end expiratory pressure defined by the user and above a preset minimum positive end expiratory pressure defined by the user.

The positive end expiratory pressure is decreased continuously and a closing pressure of the lungs is detected, if the curve of the tracing values of the volume of phase III shows a permanent gradient change after the point corresponding to the open-lung condition values, provided the closing pressure is below a preset maximum positive end expiratory pressure defined by the user and above a preset minimum positive end expiratory pressure defined by the user.

The positive end expiratory pressure is decreased continuously and a closing pressure of the lungs is detected, if the curve of the tracing values of the angle II-III shows a permanent gradient change after the point corresponding to the open-lung condition values, provided the closing pressure is below a preset maximum positive end expiratory pressure defined by the user and above a preset minimum positive end expiratory pressure defined by the user.

The positive end expiratory pressure is decreased continuously and a closing pressure of the lungs is detected, if the curve of the tracing values of the intercept of phase II slope shows a permanent gradient change after the point corresponding to the open-lung condition values, provided the closing pressure is below a preset maximum positive end expiratory pressure defined by the user and above a preset minimum positive end expiratory pressure defined by the user.

Re-Opening Procedure

The peak inspiratory pressure is set 2-5 $cmH_2O$ above the value identified during the detection of the open-lung condition, provided this value is below a preset maximum peak inspiratory pressure defined by the user and above a preset minimum peak inspiratory pressure defined by the user.

The positive end expiratory pressure is set 2-3 $cmH_2O$ above the value identified during the detection of the lung re-collapse condition, provided this value is below a preset maximum positive end expiratory pressure defined by the user and above a preset minimum positive end expiratory pressure defined by the user.

The peak inspiratory pressure is set to a value to achieve the desired tidal volume, provided this value is below a preset maximum peak inspiratory pressure defined by the user and above a preset minimum peak inspiratory pressure defined by the user.

Figure 13:
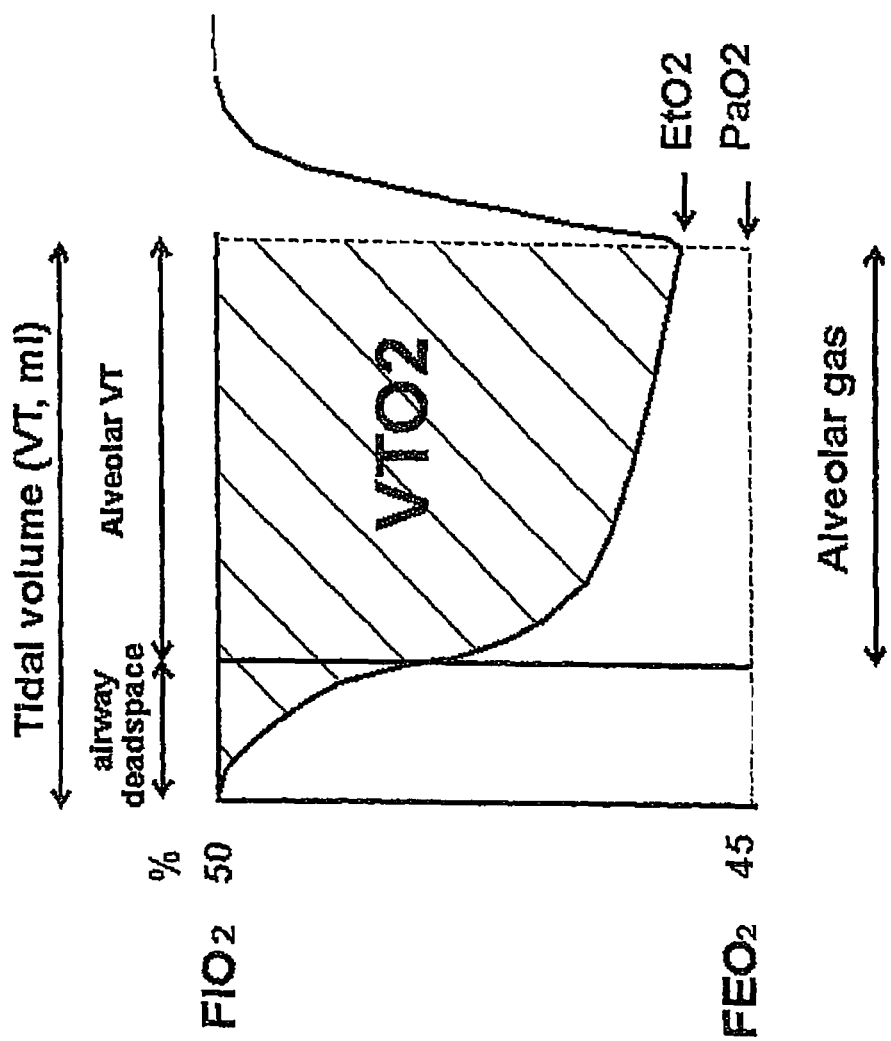
FIG. 13 shows a plot of the $O_2$ single breath test depicting the $O_2$ gas concentration during the patient exhale cycle.

FIG. 13 shows a plot of the $O_2$ single breath test depicting the $O_2$ gas concentration during the patient exhale cycle. Plotted is the expiratory oxygen fraction in percentage against time and a volume rate measurement against time. This plot corresponds to the $O_2$ single breath test. The plotted exhale cycle can be subdivided into two stages, one representing the airway dead space and the other one representing the alveolar tidal volume. The expiratory oxygen fraction does not decrease considerably within the first stage, since the gas expired represents gas from the airway conduction structures where gas exchange does not occur. On the other side, the expiratory oxygen fraction is considerably lower in the second stage, when unmixed gas from regions of the lung which normally are in active exchange with the alveolar tissue is expired. Within FIG. 13 paO2 is the partial pressure of oxygen and etO2 is the endtidal oxygen concentration of a single breath.

The plot according to FIG. 13 is formed by the exhaled partial pressure of $O_2$ against the expiratory tidal volume. Its analysis can be performed, e.g., using a fast side-stream or main-stream oxygen sensor. Furthermore, a computer is provided to record and analyze data.

The side-stream $O_2$ signal has a time delay with respect to the flow signal. A corresponding software can correct the $O_2$ delays automatically using mathematical algorithms. The $VTO_{2,br}$ or area under the curve can be computed by integrating expired flow and $O_2$ in each breath. Analysis of dead space can be done on-line and/or off-line using Fowler's analysis and adding arterial $PO_2$ values to the $O_2$ curve of the single breath test.

Figure 14:
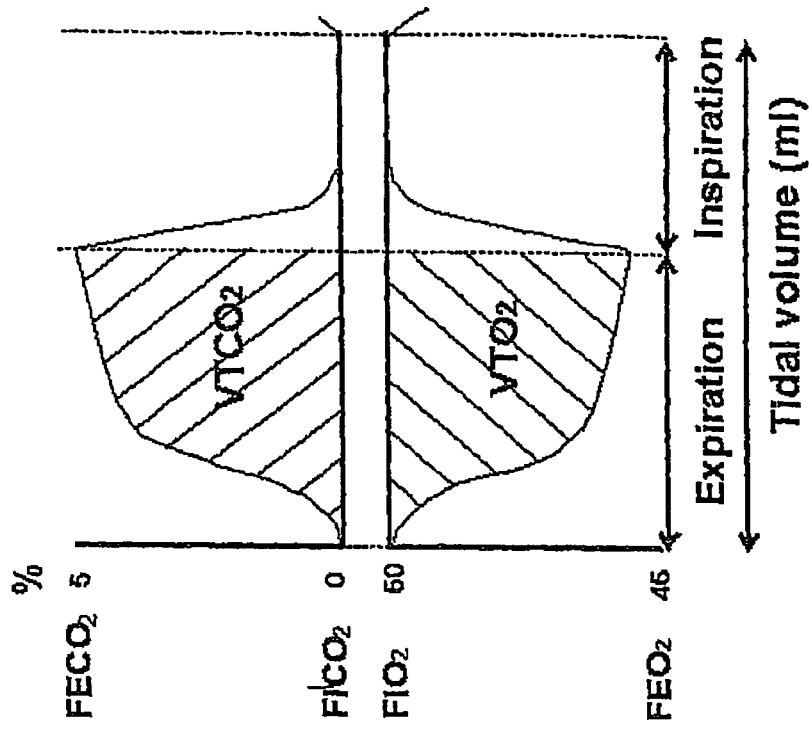
FIG. 14 shows a plot comparing the $CO_2$ gas concentration during a $CO_2$ single breath test with the $O_2$ gas concentration during an $O_2$ single breath test during the patient exhale cycle.

FIG. 14 shows a plot comparing the $CO_2$ gas concentration during a $CO_2$ single breath test with the $O_2$ gas concentration during an $O_2$ single breath test during the patient exhale cycle. As can be clearly seen, the curve of the $O_2$ single breath test looks like a mirror image of the curve of the $CO_2$ single breath test. Whereas, in this example simultaneous measurements of the $CO_2$ gas concentration and the $O_2$ gas concentration during a single breath test were performed, usually it is sufficient to perform measurements of only one gas concentration to determine the status of the lung according to the invention.

Figure 15:
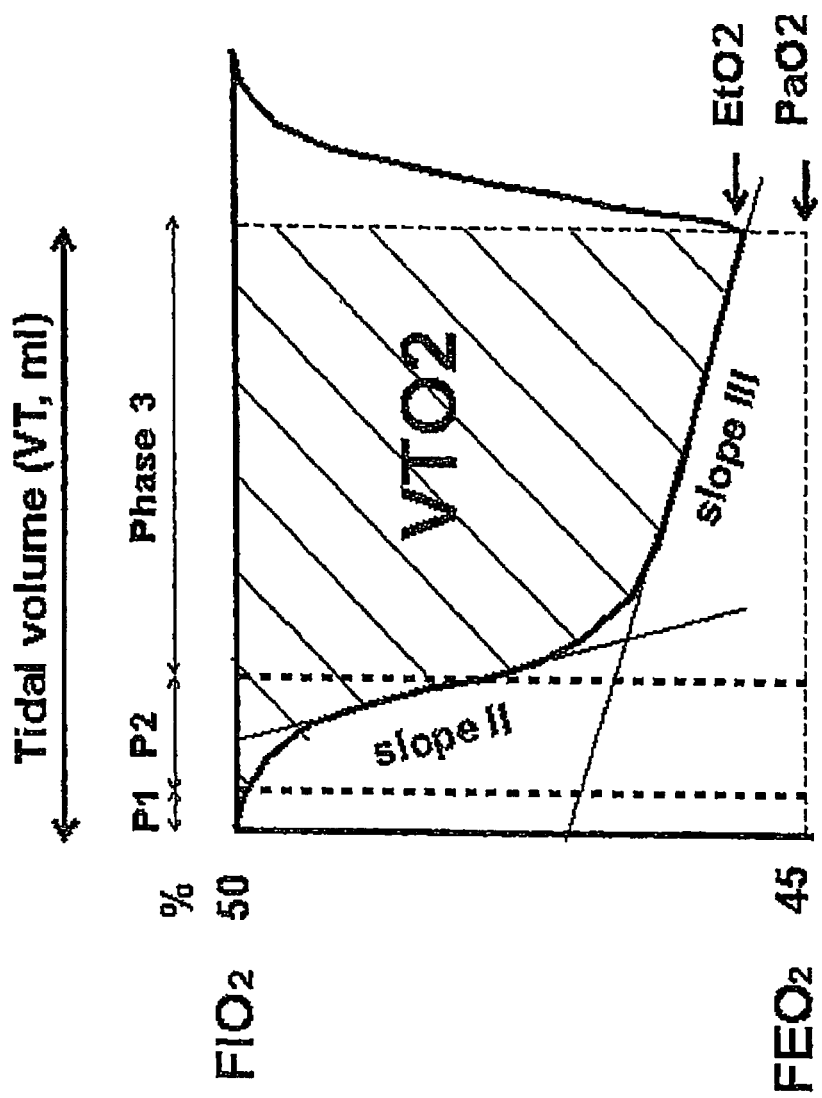
FIG. 15 shows some possible tracing values within a plot of an $O_2$ single breath test.

FIG. 15 shows some possible tracing values within a plot of an $O_2$ single breath test. As already mentioned, principally any gas concentration can be used within the method and apparatus according to the invention, provided this gas concentration allows to determine the status of the lung in accordance with the invention. In addition to is the example given so far, namely to utilize the $CO_2$ concentration, FIG. 15 demonstrates that the $O_2$ concentration can be used equally well.

In order to determine the required tracing values, the curve shown in FIG. 15 is divided into three phases. Phase I represents $CO_2$ free gas expired from the airway conduction structures where gas exchange does not occur. Hence, the $O_2$ concentration is highest and remains comparatively constant. Phase II is characterized by an counter-S-shaped downswing and represents the transition from airway to alveolar gas. Phase III reflects the exhalation of unmixed gas from regions of the lung which normally are in active exchange with the alveolar tissue and thus closely resembles at least in healthy patients gas properties associated with arterial blood in contact with the lung for gas exchange, i.e. $CO_2$ release and $O_2$ absorption. In normal lungs, Phase III is characterized by a horizontal level since ventilated and perfused alveolar regions are closely matched. In a diseased lung, Phase III may not appear horizontal due to a mismatch in ventilation and perfusion of this lung region.

FIG. 15 shows only two possible tracing values within a plot of the $O_2$ single breath test, which are

| | |
|---|---|
| slope II or steepest mean slope | determined by the steepest mean slope (either over time or over volume) of the $O_2$ concentration in the expired gas in vicinity of the point of inflection, and |
| slope III or endtidal mean slope | determined by the mean slope (either over time or over volume) of the $O_2$ concentration in the expired gas towards the final stage of a single breath. |

However, the same types of tracing values as obtained from a $CO_2$ single breath test can be determined from FIG. 15. The two presented mean tracing values can be obtained in the same way as described for the $CO_2$ single breath test with reference to FIG. 6.

It should be noted with reference to FIG. 14, that certain tracing values will have opposite signs when performing an $O_2$ single breath test compared to corresponding values obtained from a $CO_2$ single breath test.

According to the invention, a gas concentration can be used to determine the status of the lung, i.e. the $O_2$ gas concentration or the $CO_2$ gas concentration. However, the results of the evaluation of an $O_2$ single breath test according to FIG. 15 could be combined with the results of an evaluation of a $CO_2$ single breath test. This would increase the accuracy of the diagnostic method considerably.

ABBREVIATIONS

ARS alveolar recruitment strategy
BTPS ambient pressure and water vapor saturation
DLT double lumen tube
EELV end-expiratory lung volume
etCO$_2$ endtidal $CO_2$ concentration
FaeCO$_2$ mean expired alveolar fraction of $CO_2$
FiO$_2$ inspired oxygen fraction
FIR finite impulse response
OLV one-lung ventilation
paCO$_2$ partial pressure of $CO_2$
paeCO$_2$ mean alveolar fraction of $CO_2$
paO$_2$ partial pressures of oxygen
PEEP positive end-expiratory pressure
PIP peak inspiratory pressure
RQ respiratory quotient
RR respiratory rate
slope II steepest mean slope
slope III endtidal mean slope
SO$_2$ hemoglobin oxygen saturation
TLV intermittent ventilation
V/Q ventilation/perfusion relationship
VCO$_2$ carbon dioxide elimination
VD$^{alv}$ alveolar dead space
VD$^{aw}$ airway dead space
VD$^{phy}$ physiological dead space
VO$_2$ oxygen consumption
VT tidal volume
VT$^{alv}$ alveolar tidal volume
VTCO$_{2,br}$ expired volume of $CO_2$ per breath
VTe expired tidal volume
ZEEP positive end-expiratory pressure

The invention claimed is:

1. Method for providing ventilatory settings with regard to airway pressure levels of an artificial ventilator, said artificial ventilator is connectable to a lung,
comprising the steps of:
a) obtaining data samples of gas concentration of an expired gas over a single breath, said data samples of gas concentration comprising of gas originating from an airway and/or alveoli of a lung;
b) selecting a plurality of data samples from obtained data samples from step a) excluding data samples representing airway gas only;
c) calculating a tracing value being sensitive to changes of alveolar dead space on a basis of selected data samples from said step b), wherein the tracing value is represented by an angle between an endtidal mean slope of the gas concentration in the expired gas and a steepest mean slope of the gas concentration in the expired gas during the single breath;
d) changing at least one airway pressure level of the artificial ventilator and then repeating steps a), b) and c) for obtaining a plurality of tracing values; and
e) observing a resulting course of the plurality of tracing values during a course of a sequential increase of a peak inspiratory pressure of the artificial ventilator followed by a sequential decrease of a positive end expiratory pressure, and from the observation of the resulting course, detecting airway pressure levels at which alveolar opening or lung overdistension or lung open condition or alveolar closing occurs;
wherein the gas concentration represents a $CO_2$ concentration; and
wherein when the peak inspiratory pressure of the artificial ventilator is increased continuously, a lung opening is detected if the angle reaches a maximal decrease, and when the peak inspiratory pressure of the artificial ventilator is increased continuously, a lung overdistension is detected if the angle results in a decrease of about 10% from its previous value, and when the positive end expiratory pressure of the artificial ventilator is decreased continuously, an open-lung condition is detected if the angle results in a minimal value observed before a closing pressure is detected, and when the positive end expiratory pressure of the artificial ventilator is decreased continuously, a closing pressure of the lungs is detected if a curve of the tracing values of the angle shows a permanent gradient change after a point corresponding to open-lung condition values.

2. Method according to claim 1, wherein the data samples according to step a) are obtained in a time domain and are converted from the time domain into a volumetric domain.

3. Method according to claim 2, wherein a first ventilatory setting corresponds to a peak inspiratory pressure and wherein a second ventilatory setting corresponds to a positive end expiratory pressure.

4. Method according to claim 1, wherein a plurality of different types of tracing values for each breath are calculated in parallel and wherein from the resulting course of the plurality of different types of tracing values the peak inspiratory pressure at which alveolar opening or lung overdistension and/or the positive end expiratory pressure at which lung open condition or alveolar closing occurs are detected.

5. Method according to claim 1, wherein during a recruitment maneuver of the lung the peak inspiratory pressure is set above a peak inspiratory pressure at which alveolar opening has been detected and the positive end-expiratory pressure is set above a positive end expiratory pressure at which alveolar closing has been detected.

6. Method according to claim 1, wherein the airway pressure level at which alveolar opening or lung overdistension or lung open condition or alveolar closing occurs is detected when said resulting course of the plurality of tracing values reaches a minimum or a maximum.

7. Method according to claim 1, wherein the endtidal mean slope and the steepest mean slope of the gas concentration in the expired gas during the single breath is determined either over time or volume.

8. Method according to claim 1, wherein the endtidal mean slope is determined by the endtidal mean slope in a plot either over time or over volume of the gas concentration in the expired gas towards the final stage of a single breath.

9. Method according to claim 1, wherein the steepest mean slope is determined by the steepest mean slope in a plot either over time or over volume of the gas concentration in the expired gas in a vicinity of a point of inflection.

10. Apparatus for providing ventilatory settings with regard to airway pressure levels of an artificial ventilator, said artificial ventilator is connectable to a lung,
comprising:
a sensor for measuring samples of gas concentration in an expired gas during a single breath for several breaths;
an analog to digital converter for obtaining first data samples of said gas concentration of the expired gas over the single breath in a time domain;
data processor for selecting a plurality of second data samples from said first data samples, said data processor to exclude data samples representing airway gas only;
said data processor for calculating a tracing value being sensitive to changes of alveolar dead space on a basis of said second data samples, wherein the tracing value is represented by an angle between an endtidal mean slope of the gas concentration in the expired gas and a steepest mean slope of the gas concentration in the expired gas during the single breath; and
said data processor for detecting, during a change of at least one airway pressure level of the artificial ventilator, from a resulting course of a plurality of tracing values during a course of a sequential increase of a peak inspiratory pressure of the artificial ventilator followed by a sequential decrease of a positive end expiratory pressure, airway pressure levels at which alveolar opening or lung overdistension or lung open condition or alveolar closing occurs;
wherein the gas concentration represents a $CO_2$ concentration; and
wherein when the peak inspiratory pressure of the artificial ventilator is increased continuously, a lung opening is detected if the angle reaches a maximal decrease, and when the peak inspiratory pressure of the artificial ventilator is increased continuously, a lung overdistension is detected if the angle results in a decrease of about 10% from its previous value, and when the positive end expiratory pressure of the artificial ventilator is decreased continuously, an open-lung condition is detected if the angle results in a minimal value observed before a closing pressure is detected, and when the positive end expiratory pressure of the artificial ventilator is decreased continuously, a closing pressure of the lungs is detected if a curve of the tracing values of the angle shows a permanent gradient change after a point corresponding to open-lung condition values.

11. Apparatus according to claim 10, wherein said data processor is further configured for assessing a volumetric rate of the expired gas and for converting the first data samples from a time domain to a volumetric domain.

12. Apparatus according to claim 11, wherein a first ventilatory setting corresponds to a peak inspiratory pressure and wherein a second ventilatory setting corresponds to a positive end expiratory pressure.

13. Apparatus according to claim 10, wherein a plurality of different types of tracing values are calculated in parallel and wherein from the resulting course of the plurality of different types of tracing values the peak inspiratory pressure at which alveolar opening or lung overdistension and/or the positive end expiratory pressure at which lung open condition or alveolar closing occurs are detected.

14. Apparatus according to claim 10, wherein during a recruitment maneuver of the lung the peak inspiratory pressure is set above a peak inspiratory pressure at which alveolar opening has been detected and the positive end-expiratory pressure is set above a positive end expiratory pressure at which alveolar closing has been detected.

15. Apparatus according to claim 10, wherein said data processor is further configured for detecting the airway pressure level at which alveolar opening or lung overdistension or lung open condition or alveolar closing occurs when said resulting course of the plurality of tracing values reaches a minimum or a maximum.

16. Method according to claim 10, wherein the endtidal mean slope and the steepest mean slope of the gas concentration in the expired gas during the single breath is determined either over time or volume.

17. Method for providing ventilatory settings with regard to airway pressure levels of an artificial ventilator, said artificial ventilator is connectable to a lung,
comprising the steps of:
a) obtaining data samples of gas concentration of an expired gas over a single breath, said data samples of gas concentration comprising of gas originating from an airway and/or alveoli of a lung;
b) selecting a plurality of data samples from obtained data samples from step a) excluding data samples representing airway gas only;
c) calculating a tracing value being sensitive to changes of alveolar dead space on a basis of selected data samples from said step b), wherein the tracing value consists of an angle of intersection between a first slope of a first phase and a second slope of a second phase of the gas concentration in the expired gas during the single breath, wherein the first slope of the first phase consists of an endtidal mean slope which is determined by the endtidal mean slope in a plot either over time or over volume of the gas concentration in the expired gas towards the final stage of the single breath, and wherein the second slope of the second phase consists of a steepest mean slope which is determined by the steepest mean slope in a plot either over time or over volume of the gas concentration in the expired gas in a vicinity of a point of inflection;

d) changing at least one airway pressure level of the artificial ventilator and then repeating steps a), b) and c) for obtaining a plurality of tracing values; and e) observing a resulting course of the plurality of tracing values during a course of a sequential increase of a peak inspiratory pressure of the artificial ventilator followed by a sequential decrease of a positive end expiratory pressure, and from the observation of the resulting course, detecting airway pressure levels at which alveolar opening or lung overdistension or lung open condition or alveolar closing occurs;

wherein the gas concentration represents a $CO_2$ concentration; and wherein when the peak inspiratory pressure of the artificial ventilator is increased continuously, a lung opening is detected if the angle reaches a maximal decrease, and when the peak inspiratory pressure of the artificial ventilator is increased continuously, a lung overdistension is detected if the angle results in a decrease of about 10% from its previous value, and when the positive end expiratory pressure of the artificial ventilator is decreased continuously, an open-lung condition is detected if the angle results in a minimal value observed before a closing pressure is detected, and when the positive end expiratory pressure of the artificial ventilator is decreased continuously, a closing pressure of the lungs is detected if a curve of the tracing values of the angle shows a permanent gradient change after a point corresponding to open-lung condition values.

18. Apparatus for providing ventilatory settings with regard to airway pressure levels of an artificial ventilator, said artificial ventilator is connectable to a lung, comprising:

a sensor for measuring samples of gas concentration in an expired gas during a single breath for several breaths;

an analog to digital converter for obtaining first data samples of said gas concentration of the expired gas over the single breath in a time domain;

data processor for selecting a plurality of second data samples from said first data samples, said data processor to exclude data samples representing airway gas only;

said data processor for calculating a tracing value being sensitive to changes of alveolar dead space on a basis of said second data samples, wherein the tracing value consists of an angle of intersection between a first slope of a first phase and a second slope of a second phase of the gas concentration in the expired gas during each single breath, wherein the first slope of the first phase consists of an endtidal mean slope which is determined by the endtidal mean slope in a plot either over time or over volume of the gas concentration in the expired gas towards the final stage of the single breath, and wherein the second slope of the second phase consists of a steepest mean slope which is determined by the steepest mean slope in a plot either over time or over volume of the gas concentration in the expired gas in a vicinity of a point of inflection;

said data processor for detecting, during a change of at least one airway pressure level of the artificial ventilator, from a resulting course of a plurality of tracing values during a course of a sequential increase of the peak inspiratory pressure of the artificial ventilator followed by a sequential decrease of the positive end expiratory pressure, airway pressure levels at which alveolar opening or lung overdistension or lung open condition or alveolar closing occurs;

wherein the gas concentration represents a $CO_2$ concentration; and wherein when the peak inspiratory pressure of the artificial ventilator is increased continuously, a lung opening is detected if the angle reaches a maximal decrease, and when the peak inspiratory pressure of the artificial ventilator is increased continuously, a lung overdistension is detected if the angle results in a decrease of about 10% from its previous value, and when the positive end expiratory pressure of the artificial ventilator is decreased continuously, an open-lung condition is detected if the angle results in a minimal value observed before a closing pressure is detected, and when the positive end expiratory pressure of the artificial ventilator is decreased continuously, a closing pressure of the lungs is detected if a curve of the tracing values of the angle shows a permanent gradient change after a point corresponding to open-lung condition values.

* * * * *